United States Patent [19]

Chesterfield et al.

[11] Patent Number: 5,520,084
[45] Date of Patent: May 28, 1996

[54] APPARATUS AND METHOD FOR PRODUCING BRAIDED SUTURE PRODUCTS

[75] Inventors: Michael P. Chesterfield, Norwalk, Conn.; Josep Serra, Barcelona, Spain; Ilya Koyfman, Orange, Conn.

[73] Assignee: United States Surgical Corporation, Norwalk, Conn.

[21] Appl. No.: 372,308

[22] Filed: Jan. 13, 1995

Related U.S. Application Data

[62] Division of Ser. No. 72,344, Jun. 4, 1993, Pat. No. 5,383,387, which is a continuation of Ser. No. 569,079, Aug. 17, 1990, abandoned.

[51] Int. Cl.$^6$ .............................. D04C 3/14; D04C 3/24
[52] U.S. Cl. ............................ 87/56; 87/22; 87/61
[58] Field of Search .................. 87/50, 51, 31, 87/ 32, 56, 57, 61, 62, 9, 21, 22; 254/371

[56] References Cited

U.S. PATENT DOCUMENTS

| | | |
|---|---|---|
| 776,842 | 12/1904 | Horwood . |
| 998,031 | 7/1911 | Neufeld . |
| 1,154,964 | 9/1915 | Bentley . |
| 1,285,451 | 11/1918 | Stanton . |
| 1,358,173 | 11/1920 | Penso et al. . |
| 1,442,432 | 1/1923 | Hooper . |
| 1,486,527 | 3/1924 | Larkin . |
| 1,582,055 | 4/1926 | Krissiep . |
| 1,633,346 | 6/1927 | Mossberg . |
| 1,765,117 | 6/1930 | Wright et al. . |
| 1,785,683 | 12/1930 | Mallory . |
| 1,997,210 | 4/1935 | Ford et al. ................ 96/3 |
| 2,053,161 | 9/1936 | Olson et al. ............... 96/15 |
| 2,079,836 | 5/1937 | Brown et al. .............. 96/11 |

(List continued on next page.)

FOREIGN PATENT DOCUMENTS

| | | |
|---|---|---|
| 423412 | 4/1911 | France . |
| 2482634 | 11/1981 | France . |
| 1660004 | 6/1971 | Germany . |
| 2162170 | 6/1973 | Germany . |
| 3038343 | 5/1982 | Germany . |
| 3144589 | 5/1983 | Germany . |
| 3412998 | 10/1985 | Germany . |
| 85215 | 6/1920 | Switzerland . |
| 283477 | 12/1970 | U.S.S.R. . |
| 255802 | 5/1976 | U.S.S.R. . |
| 524872 | 11/1976 | U.S.S.R. . |
| 800259 | 1/1981 | U.S.S.R. . |
| 138069 | 9/1920 | United Kingdom . |
| 375654 | 6/1932 | United Kingdom . |
| 579402 | 8/1946 | United Kingdom . |
| 836240 | 6/1960 | United Kingdom . |
| 872679 | 7/1961 | United Kingdom . |
| 871835 | 7/1961 | United Kingdom . |
| 1332591 | 10/1973 | United Kingdom . |
| 1555941 | 11/1979 | United Kingdom . |
| 2081756 | 2/1982 | United Kingdom . |

OTHER PUBLICATIONS

Published Description on Ratera Braiding Machine (date unavailable).

*Primary Examiner*—William Strysewski

[57] ABSTRACT

An apparatus is disclosed for braiding fine denier yarns to form a braided suture product which includes a frame, and a main carrier support plate supported on the frame and having a pair of undulating guide channels intersecting each other for guiding a plurality of yarn carriers. A plurality of yarn carriers are supported on the main carrier support plate, and each supports a bobbin for dispensing fine denier yarn. The yarn carriers are directed over intersecting paths corresponding to the shape of the guide channels, with a first set of the carriers being directed in a first direction and a second set of the carriers being directed in the opposite direction. The yarns are received in a common braiding zone above the yarn carriers while the yarn carriers are directed through the intersecting paths of the guide channels to form a braided sheath from the yarns. The tension of the final braided product is controlled within predetermined ranges to permit formation of a braided product of predetermined appearance. A method of producing the braided product on the inventive braiding apparatus is also disclosed.

26 Claims, 12 Drawing Sheets

U.S. PATENT DOCUMENTS

| | | | |
|---|---|---|---|
| 2,200,323 | 5/1940 | Barrans et al. | 96/3 |
| 2,337,770 | 12/1943 | Rickenbacher | 242/118 |
| 2,452,136 | 10/1948 | Marti | 87/33 |
| 2,895,371 | 7/1959 | Herzog | 87/56 |
| 2,897,715 | 8/1959 | Olson | 87/56 |
| 2,897,716 | 8/1959 | Olson | 87/57 |
| 2,986,061 | 5/1961 | Carter | 87/56 |
| 3,004,463 | 10/1961 | Griesemer | 87/56 |
| 3,038,367 | 6/1962 | Karg et al. | 87/22 |
| 3,045,526 | 7/1962 | Harris | 87/56 |
| 3,187,752 | 6/1985 | Glick | 128/335.5 |
| 3,362,283 | 1/1968 | Dergachev et al. | 87/33 |
| 3,363,502 | 1/1968 | Florentine | 87/38 |
| 3,396,625 | 8/1968 | Faulkner | 87/22 |
| 3,565,077 | 2/1971 | Glick | 128/335.5 |
| 3,783,736 | 1/1974 | Richardson | 87/29 |
| 3,817,147 | 6/1974 | Richardson | 87/57 |
| 3,854,375 | 12/1974 | Lefevre | 87/55 |
| 4,014,973 | 3/1977 | Thompson | 264/290 R |
| 4,034,643 | 7/1977 | Ianucci et al. | 87/48 |
| 4,043,344 | 8/1977 | Landi et al. | 128/335.5 |
| 4,047,533 | 9/1977 | Perciaccante et al. | 128/335.5 |
| 4,084,479 | 4/1978 | Ratera | 87/48 |
| 4,158,984 | 6/1979 | Griffiths | 87/8 |
| 4,304,169 | 12/1981 | Cimprich et al. | 87/29 |
| 4,333,380 | 6/1982 | Kozlowski | 87/6 |
| 4,574,679 | 3/1986 | Lasher | 87/87 |
| 4,716,807 | 1/1988 | Fischer | 87/20 |
| 4,736,668 | 4/1988 | Moyer | 87/57 |
| 4,753,149 | 6/1988 | Celani | 87/29 |
| 4,765,220 | 8/1988 | Ianucci et al. | 87/48 |
| 4,785,709 | 11/1988 | Freitas | 87/33 |
| 4,802,398 | 2/1989 | Champlin et al. | 387/29 |
| 4,909,127 | 3/1990 | Skelton et al. | 87/33 |
| 4,922,798 | 5/1990 | Ivsan et al. | 87/8 |
| 4,959,069 | 9/1990 | Brennan et al. | 606/228 |
| 5,019,093 | 5/1991 | Kaplan et al. | 606/228 |
| 5,059,213 | 10/1991 | Chesterfield et al. | 606/228 |
| 5,181,923 | 1/1993 | Chesterfield et al. | 606/228 |

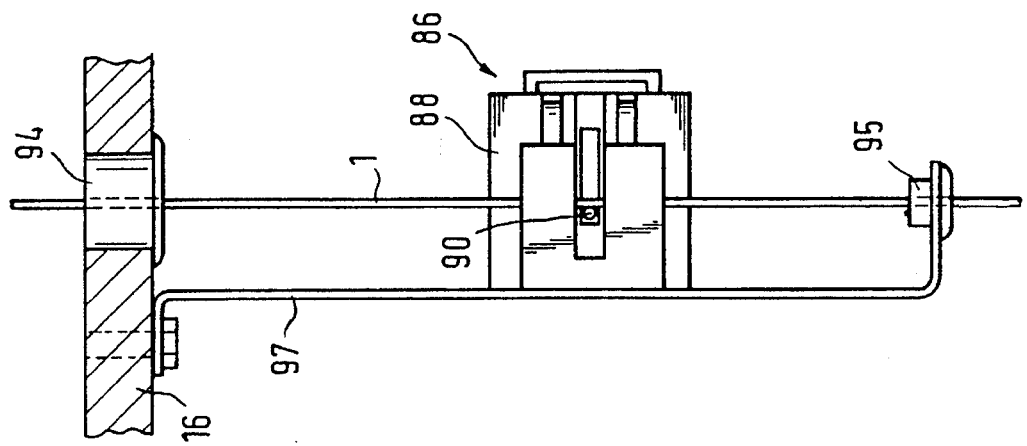
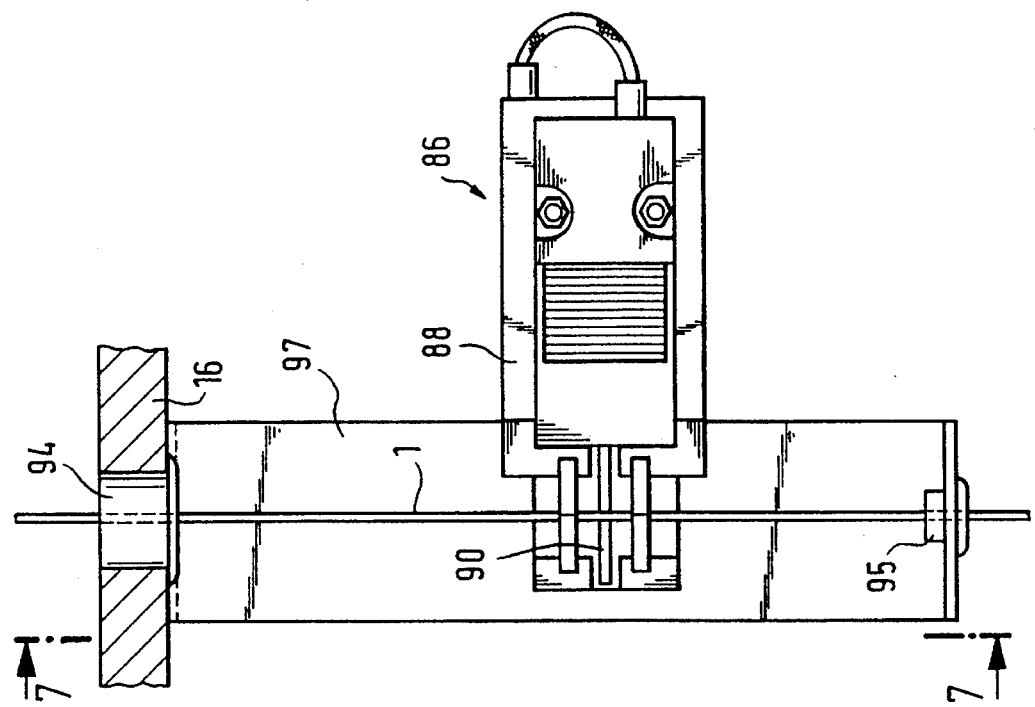
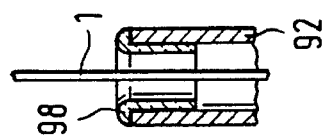
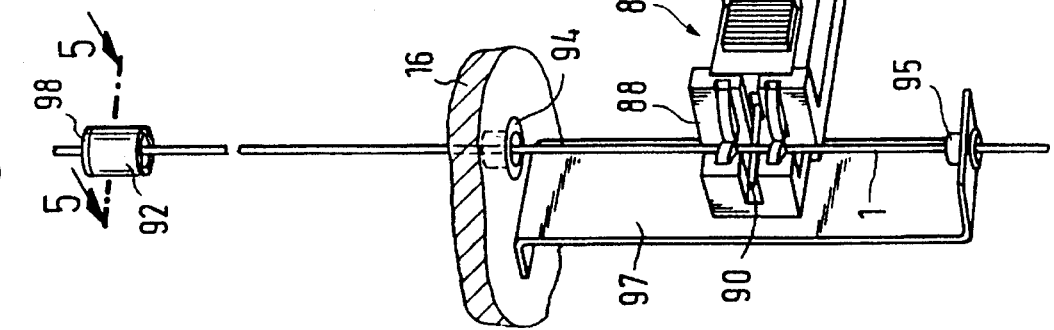

APPARATUS AND METHOD FOR PRODUCING BRAIDED SUTURE PRODUCTS

This is a divisional of application No. 08/072,344, filed Jun. 4, 1993, now U.S. Pat. No. 5,383,387, which is a file wrapper continuation of application Ser. No. 07/569,079, filed Aug. 17, 1990, now abandoned.

BACKGROUND OF THE INVENTION

1. Field of the Invention

This invention relates to an improved apparatus and method for braiding fine denier yarns into sutures for surgical applications.

2. Description of the Prior Art

Braided products and apparatus for production of such products are well-known. However, for some time now, braiding machines have been directed to production of braided products of relatively bulky sizes for uses in applications in packaging, window blind pulls, braided rope or the like. In essence, the applications for such braided products are legion.

Typical of the braiding mechanisms used for such products are disclosed in U.S. Pat. Nos. 776,842 to Horwood, 1,154,964 to Bentley, 1,285,451 to Stanton, 1,358,173 to Penso et al., 1,486,527 to Larkin, 1,785,683 to Mallory, 2,079,836 to Brown et al., 2,200,323 to Barrans et al., 2,452,136 to Marti, 4,158,984 to Griffiths, 4,304,169 to Cimprich et al., 4,333,380 to Kozlowski, 4,716,807 to Fischer, 4,753,149 to Celani, 4,909,127 to Skelton et al. and 4,922,798 to Ivsan. British Patent Publication No. 138,069 dated Sep. 2, 1920 relates to improvements in such braiding devices.

Sutures intended for the repair of body tissues must meet certain requirements: they must be substantially non-toxic, capable of being readily sterilized, they must have good tensile strength and have acceptable knot-tying and knot-holding characteristics and if the sutures are of the bio-absorbable variety, the bio-absorption of the suture must be closely controlled.

Sutures have been constructed from a wide variety of materials including surgical gut, silk, cotton, polyolefins such as polypropylene, polyamides, polyesters such as polyethylene terephthalate, polyglycolic acid, glycolide-lactide copolymer, etc. Although the optimum structure of a suture is that of a monofilament, since certain materials of construction would provide a stiff monofilament suture lacking acceptable knot-tying and knot-holding properties, sutures manufactured from such materials have been provided as braided structures. Thus, for example, sutures manufactured from silk, polyamide, polyester and bio-absorbable glycolide-lactide copolymer are usually provided as multifilament braids.

Currently available braided suture products are braided on conventional braider-carriers which travel around the perimeter of the braider deck to result in a tubular type braid with the yarns crossing over each other on the surface of the braid. In the larger sizes, e.g., 5/0 and larger, the tubular braid, or sheath, is constructed about a core structure which is fed through the center of the braider. Known tubular braided sutures, including those possessing cores, are disclosed, e.g., in U.S. Pat. Nos. 3,187,752; 3,565,077; 4,014, 973; 4,043,344; and, 4,047,533.

High speed production of braided sutures from fine denier yarns presents difficulties not encountered in connection with production of heavy duty braided products such as cord, rope or the like. In particular, it has been found that typical braiding mechanisms abrade, damage or break the fine denier filaments used to make braided sutureproducts, and reduce product yield. Moreover, many braided suture products, particularly absorbable braided sutures, are stiff and wiry and exhibit "memory" or "sets". Recent attempts to improve the flexibility, hand and tissue drag characteristics of braided sutures have resulted in new braid structures possessing a significantly greater number of sheath yarns for a given overall denier, the sheath yarns being fabricated from individual filaments of finer denier than filaments which are typical of known types of braided sutures. Braided sutures of this type are disclosed and claimed In U.S. patent application Serial No. 419,215 filed Mar. 9, 1990 and prior related applications. While it is possible to produce such structures on conventional braiders, applicants were able to do so at a maximum production rates approaching only about 6 meters per hour.

The present invention relates to improvements in such apparatus and methods for continuously braiding fine denier yarns into fine braided products having predetermined construction and appearance suitable for use in body tissue repair. More specifically, the present invention makes it now possible to produce the preferred braided sutures at relatively high speeds on the order of about 13 to 15 meters per hour.

SUMMARY OF THE INVENTION

The present invention relates to improvements in apparatus for braiding elongate flexible members to form a final braided product. The braided product may be of the type formed only of a braided sheath or it may be of the type wherein braided sheath is formed about a center core. In particular, the present invention is directed to improvements which make it possible to produce a braided product from fine denier yarns of sizes applicable to sutures for surgically repairing body tissue. Such braided suture products have been found to have improved handling characteristics while exhibiting improved knot run-down and tissue drag characteristics. For these reasons there has been a long felt need to produce such braided sutures. However, to date braiding technology has not been developed to the level where such braided products with the desirable properties for suture applications have been made possible. The present invention is directed to such improvements in braiding technology.

The present invention is directed generally to the following aspects of braiding apparatus:

1) core tensioning—detection and control;

2) core guiding;

3) braider bobbins and yarn dispensing;

4) yarn carrier technology;

5) braider gearing technology; and 6) braided product guiding, wind up and control.

The improvements of the present invention make it possible to produce a braided product from fine denier sheath yarns of suture application size, i.e. delicate yarns from 0.2 to 6.0 denier weight and, optionally, a core preferably from about 50 to about 2500 denier. With such yarns it has been found necessary to structure the yarn dispensing and yarn take-up systems in a manner which makes consistent, uniform braiding of the yarns at high speed now possible. For example, a typical prior art yarn bobbin empty of yarns weighed 50 grams or more and had 12 or more radial segments at the lower end for controlling yarn tension. The yarn bobbin of the present invention weighs about 20–22 grams without yarns and contains 9–11 segments to facilitate high speed operation. Contrary to normal expectations, the diameter of bobbins in accordance with the invention is greater than the diameter of prior braider bobbins in order to increase control over the fine denier yarns. In addition, the bobbin is of unitary injection molded plastic construction to improve weight distribution and precision in unwinding of yarn. Other improvements herein relate to tension control and yarn and product take-up control for reducing abrasion to the filaments during braiding in order to produce a product having predetermined characteristics and features while each of the components forming the product is suitably layed-in and appropriately pre-tensioned to provide a product of the desired braid construction.

The present invention relates to an apparatus for braiding fine denier yarns which comprises frame means, means associated with the frame means for supporting a plurality of bobbins containing fine denier yarns, means for directing the plurality of bobbins through intersecting undulating paths while dispensing yarn from each bobbin toward a common braiding zone to form an elongated sheath of braid construction, and means to control the tension on the finished braided product within predetermined limits to permit braiding the yarns in a manner to have a predetermined construction and appearance.

In a preferred embodiment, the apparatus for braiding fine denier yarns to form a braided suture product comprises frame means, a main carrier support plate having a pair of undulating guide channels intersecting each other for guiding a plurality of yarn carriers, a plurality of yarn carriers supported on the main carrier support plate, each supporting a bobbin for dispensing fine denier yarn, means for directing the yarn carriers over intersecting paths corresponding to the shape of the guide channels, a first set of the carriers being directed in a first direction and a second set of the carriers being directed in the opposite direction, means positioned above the yarn carriers for reception of the yarns in a common braiding zone while the yarn carriers are directed through the intersecting paths to form a braided sheath from the yarns, and means for controlling the tension of the final braided product within predetermined ranges to permit formation of a braided product of uniform predetermined construction and appearance.

The apparatus includes a plurality of individual carrier support plates supported on the main carrier support plate. Each individual carrier support plate includes means positionable within at least one of the guide channels for guiding the carrier support plate along at least a portion of a path defined by the guide channel. The individual carrier support plates are supported by a plurality of carrier support and transfer plates positioned adjacent each other and adapted for rotation. Further, each carrier support and transfer plate is geared for rotation in a direction opposite the direction of rotation of the next adjacent carrier support and transfer plate. The carrier support and transfer plates are disposed adjacent each other along a circular path. The carrier support plates each contain at least two downwardly extending guide members dimensioned and configured to be positioned within one of the guide channels in the main carrier support plate for guiding the individual carrier support plate and the carrier along a path defined by the guide channel.

Each carrier support and transfer plate defines four cut-out portions spaced 90° from each other for reception of a yarn carrier as the individual carrier support plates rotate adjacent each other. Further, each individual carrier support and transfer plate is arranged to receive a member attached to the individual carrier support plates for at least one of a first set of carriers within a cut—out portion to cause the carrier to travel with the cut—out portion approximately 180° rotation of the carrier support and transfer plate for transfer of the carrier to a next adjacent individual carrier support plate rotating in a direction opposite the first carrier support plate whereby the carrier traverses an undulating path as defined by one of the guide channels in the main carrier support plate as the carrier is transferred from each carrier support and transfer plate to the next adjacent carrier support and transfer plate. Each carrier support and transfer plate is arranged to receive a member attached to the individual carrier support plate of at least one of a second set of carriers within the cut-out portions in a manner to cause each of the second set of carriers to traverse the second of the undulating paths defined by the guide channels in the main carrier support plate such that the second set of yarn carriers traverses a path which intersects with the path followed by the first set of yarn carriers in a direction opposite the first set of carriers.

Each yarn carrier includes an upstanding spindle to support a yarn bobbin for rotation of the bobbin for dispensing yarn as the bobbins traverse the undulating pathswith the carriers. The vertical spindle includes means at the upper end portion for releasably retaining the bobbin on the spindle while permitting the bobbin to rotate as yarn is selectively dispensed therefrom. Preferably, the releasable bobbin retention means is a clip positioned at the upper end portion of the spindle and having a member extending therefrom resiliently biased toward a position which interferes with upward movement of the bobbin on the spindle so as to retain the bobbin in position on the spindle. The clip includes a resilient spring which biases the clip against upward movement with respect to the spindle so as to permit release of the clip from the position of interference with the bobbin. Also, the clip is resiliently movable from a first position in interference with the upward bobbin movement to a second position which permits removal of the bobbin from the spindle. The bobbin is of lightweight construction, on the order of about 20 grams in weight, and preferably is made from injection molded nylon. Further, the bobbin is rotatable on the spindle for dispensing yarns to the braiding zone, and each individual yarn carrier includes means for selectively preventing rotation of the bobbin and for selectively permitting rotation of the bobbin in dependence on the tension in the yarn. A pivotal arm having yarn guide means for guiding yarn from the bobbin to the braiding zone is provided. Also, a plurality of radial segments are positioned at least about the lower surface of the bobbin and the pivotal arm is connected to an upstanding pawl arranged to enter into a space defined between the radial segments on the bobbin in dependence upon the tension in the yarn so as to prevent rotation of the bobbin in dependence upon the tension in the yarn and to permit withdrawal of the pawl from the space when the yarn tension exceeds a predetermined value. The pivotal arm is resiliently biased against pivotal movement which causes withdrawal of the pawl from a space between the segments on the bobbin. The end of the pivotal arm engages a coil spring when the yarn tension is within a range of about 5 to 7 grams. The coil spring preferably has a spring rate of from about 0.6 to 0.7 pounds per inch to accommodate fine denier yarns.

The yarn is arranged to be dispensed from the bobbin and to extend to the yarn guide means on the carrier in a manner to lift one end of the pivotal arm when the yarn tension exceeds a predetermined value so as to cause withdrawal of the pawl from the space defined by the radial segments on the bobbin, thereby permitting rotation of the bobbin as the yarn is drawn therefrom by the tension produced at the braiding zone. Each bobbin is structured to have a diameter above a predetermined value to maintain the moment for rotating the bobbin about the spindle above a predetermined value. Each bobbin contains a minimum number of pawl engaging segments on the lower surface thereof to maintain the spaces between the segments at a substantial level sufficient to facilitate high speed rotation of the bobbin about the spindle. Each bobbin preferably contains between 9 and 11 pawl engaging segments on the lower surface.

A pair of take-up rollers is positioned downstream of the braiding zone for directing finished braided product toward a take-up spool for winding thereabout. Each of the take-up rollers has a plurality of substantially parallel grooves having a V-shaped cross-sectional configuration for reception of braided products of a plurality of sizes. The take-up rollers are constructed of a lightweight plastic material, i.e. nylon. Further, the take-up rollers are of machined construction having surfaces substantially devoid of imperfections to avoid abrading or snagging of the suture product.

A take-up clutch means is provided to control tension on the finished braided product. Also, a take-up spool is arranged for rotation on a take-up spindle for reception of finished braided product. The take-up clutch means is connected to the take-up spindle to adjust the tension on the finished braided product. The take-up clutch means preferably comprises a pulley wheel connected for belt driven rotation and friction plates in contacting relation therewith. The friction plates are connected to the take-up spindle, and means are provided to adjust the friction forces between the friction plates with respect to the pulley wheel to selectively control the tension on the finished product. The take-up spindle includes means for quick lock/release of the take-up spool with respect to the spindle. The quick lock/release means comprises an elongated member slidably positioned within an opening at the end portion of the take-up spindle. The elongated member is movable between a first position in line with the central opening of the take-up spool whereby removal of the take-up spool is facilitated, and a second position transverse of the take-up spindle which interferes with removal of the take-up spool from the take-up spindle. The elongated member is a generally elongated plate having a slot extending over a portion of the length of the plate and the spindle defines a slot for slidable reception the elongated plate. The spindle contains a pin extending transversely of the slot in the end portion thereof for positioning within the slot defined in the elongated plate such that the plate can be slidably positioned between the first position generally aligned with the spindle and the second position transverse of the spindle while the retains the slotted plate connected to the end portion of the spindle.

Means are provided for dispensing a fine denier core yarn at a location such that the sheath yarns are braided thereabout. The preferred core yarn is from about 50 to 2500 denier. The means for dispensing the core yarn is preferably in the form of a spool of core yarn rotatably mounted below the main carrier support plate for directing the core yarn upwardly through a central opening in the main carrier plate whereby the sheath yarns are braided in the form of a braided sheath about the core yarn. The core yarn spool is mounted for rotation about a spindle, the spindle being longitudinally positioned below the main carrier support plate. Means are provided to control the tension on the core yarn. The tension controlling means preferably comprises a grooved member connected for rotation with the core yarn spool and a fixed flexible elongated member positioned about the grooved member within the groove, and weighted means connected to the flexible member to permit selectively increasing or decreasing friction between the flexible member and the grooved member to selectively increase or decrease the tension on the core yarn as the core yarn is dispensed.

Means are preferably positioned in engagement with the core yarn for detecting tension in the core yarn. The core yarn tension detecting means is adapted to measure tension in the core-yarn between about 25 and 80 grams. Electrical power means is provided to rotatably drive the yarn carrier support and transfer plates and the braided yarn take-up means. Each carrier support and transfer plate, or "horn gear", rotates at a rate of about 50 to about 500 revolutions per minute, and preferably about 350 revolutions per minute. The core yarn tension detector is adapted to discontinue electrical power to the apparatus in the event of reduction of tension in the core yarn due breakage of the core yarn.

A core tube extends from the main carrier support plate vertically upward to a location below the braiding zone for guiding the core yarn toward the braiding zone. The core tube includes a ceramic yarn guide member positioned at each end for guiding the core yarn upwardly from the core yarn spool to a location generally adjacent the braiding zone.

In an alternate embodiment, the pulley wheel of the suture tensioning clutch is of two-part construction, an inner and an outer part. The outer part is mounted by bearing means on the inner part for relative rotation. The bearing means is preferably a ball bearing unit. The take-up rollers are gear driven to each other. Alternatively, the take-up rollers are belt driven to each other.

A method is also disclosed for braiding fine denier yarns comprising directing a plurality of fine denier yarns through a plurality of intersecting paths and toward a common braiding zone so as to form an elongated sheath of braid construction, and applying controlled tension on the finished braided product to permit braiding of the yarns in a manner to have a predetermined construction and appearance.

Preferably, the method for braiding fine denier yarns to form a braided suture product comprises supporting a plurality of yarn carriers containing fine denier yarns in a manner to permit selective dispensing of yarns therefrom, directing the yarn carriers over intersecting paths such that a first set of the carriers is directed in a first direction and a second set of the carriers is directed in the opposite direction, receiving the yarns in a common braiding zone located above the carriers in a manner to permit formation of a braided sheath of the yarns, and controlling the tension on the final braided yarn product within predetermined ranges to permit formation of a braided yarn product of predetermined appearance.

In the preferred embodiment, the yarn carriers are supported on a main carrier support plate having a pair of undulating guide channels intersecting each other for guiding the yarn carriers over intersecting paths and each yarn carrier is arranged to support an individual yarn bobbin. The main carrier support plate is provided with a plurality of undulating guide channels and the yarn carriers are each supported on an individual carrier support plate. Each individual carrier support plate has means for guiding the carrier support plate over at least one of the paths defined by the channels in the main carrier support plate. A plurality of carrier support plates are provided to transfer the carriers. The carrier support plates are each rotated in directions opposite the direction of rotation of the next adjacent carrier support plate. Further, the individual carrier support plates are guided over the intersecting paths defined by the guide channels while dispensing yarn from the individual yarn carriers. Each yarn bobbin is rotatably supported on the individual yarn carrier.

The method further comprises selectively permitting rotation of each yarn bobbin in dependence on the tension of the yarn being dispensed therefrom by preventing each yarn bobbin from rotating and dispensing yarn when the tension in the yarn is between about 5 and 7 grams. Further, each yarn bobbin is permitted to rotate when the yarn tension is above about 5 grams. The method also comprises winding the finished braided yarn suture product on take-up rollers at predetermined rotational speeds positioned downstream of the braiding zone. The winding is accomplished on a take-up spool adapted for rotation and for taking up the finished braided product while controlling the rotational speed of the take-up spool for controlling the tension on the braided yarn product during formation thereof.

The method further comprises controlling the tension on the braided suture product during formation by providing clutch braking on the product take-up spool and directing a core yarn into the braiding zone in a manner so as to facilitate formation of the braided suture product about the core yarn. Predetermined tension is applied to the core yarn between about 75 and 80 grams.

According to the method, the core yarn is between about 50 and about 2500 denier, the sheath yarns are between about 10 and about 100 denier, and the overall denier of the finished braided suture product is betweenabout 50 and about 4000 denier.

BRIEF DESCRIPTION OF THE DRAWINGS

Preferred embodiments of the invention will be described hereinbelow with reference to the drawings wherein:

FIG. 4 is a perspective view from below, with parts broken away, of the core tension detection system and the core tube which form part of the present invention;

FIG. 5 is a cross-sectional view taken along lines 5—5 of FIG. 4 illustrating the novel core tube construction;

FIG. 6 is an elevational view of the core tension control and ceramic eyelet system of the invention for controlling the core input feed;

FIG. 7 is a cross-sectional view taken along lines 7—7 of FIG. 6;

DETAILED DESCRIPTION OF THE PREFERRED EMBODIMENTS

Figure 1:
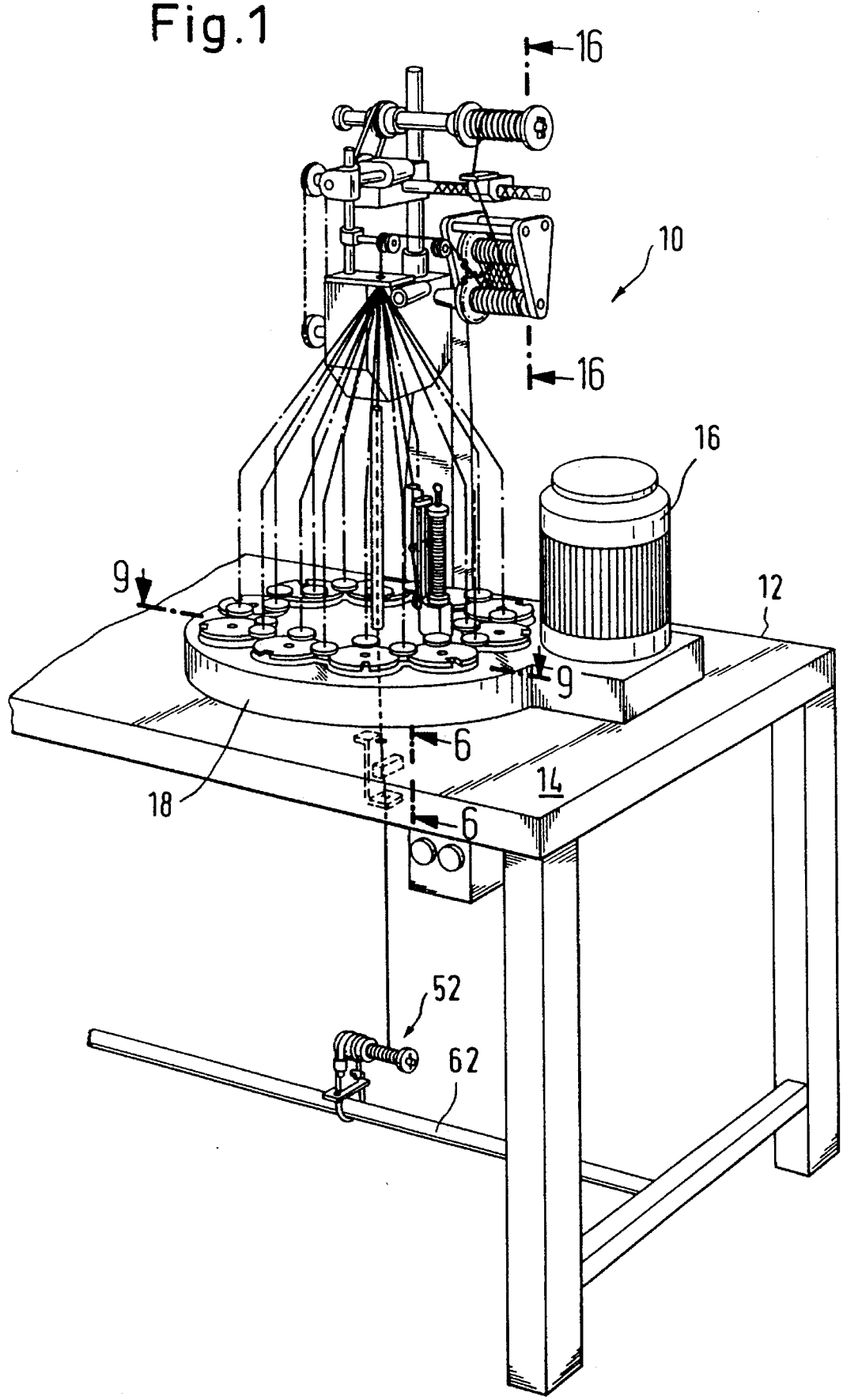
FIG. 1 is a frontal perspective view of the apparatus for braiding fine denier yarns constructed according to the present invention.

Referring initially to FIG. 1, there is illustrated an apparatus 10 for braiding sutures constructed according to the present invention. The apparatus 10 is supported on frame 12 which includes horizontal support plate 14 as shown. Electrically powered motor 16 is arranged to drive the apparatus as will be described.

Figure 8:
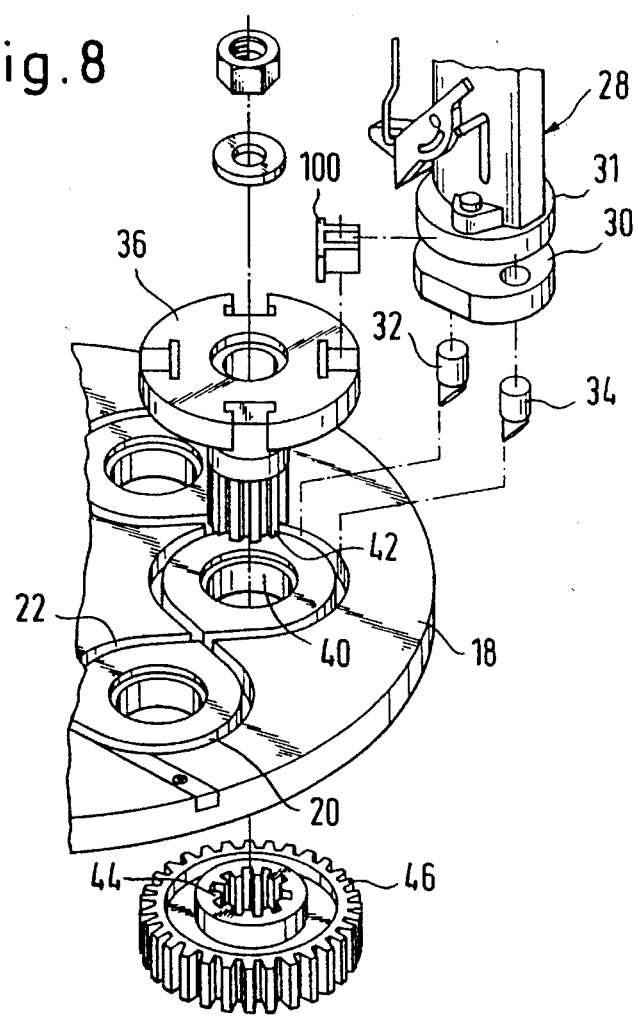
FIG. 8 is a perspective view with parts broken away, of the horn gear system of the invention for promoting noise reduction.
Figure 9:
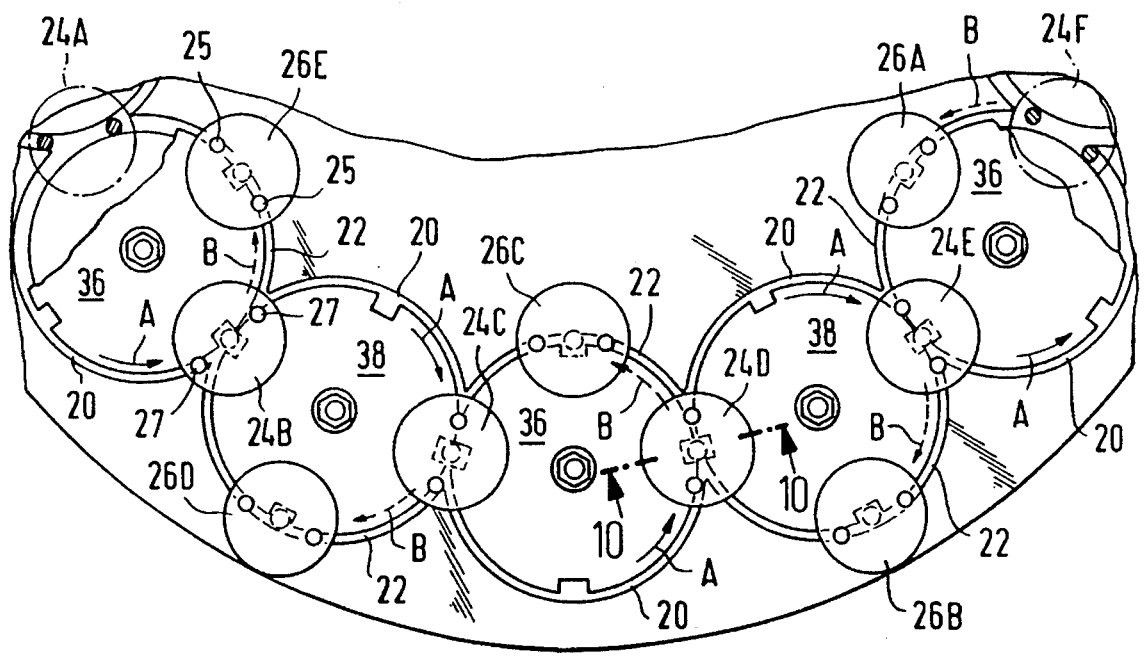
FIG. 9 is a plan view from above, with parts broken away for convenience of illustration, of the horn gear noise reduction system shown in FIG. 8.

Referring now to FIGS. 8 and 9 in conjunction with FIG. 1, the apparatus includes main carrier support plate 18 which defines a pair of tortuous endless intersecting guide channels 20 and 22 which extend therearound as shown. Each channel has a set of yarn carriers guided therein with those of the yarn carriers in channel 20 designated carriers 24A, 24B, 24C, 24D, 24E and 24F, and those carriers in channel 22 designated carriers 26A, 26B, 26C, 26D, 26E. Each series of carriers is arranged to move in opposite directions while yarn is selectively dispensed from the selectively intermittently rotating bobbins associated therewith to form the braided suture. The path of the carriers through guide channel 20 is illustrated by the arrows A and the path of the carriers through guide channel 22 is illustrated by dotted arrows B.

The mechanism for effecting this movement of the carriers is illustrated in FIG. 8. The carriers 28 each include an individual carrier support plate 30 to which is connected a pair of connector shoes 32, 34 which are positionable within, and traverse the respective guide channel 20, 22 in a manner to be described. A series of carrier support and transfer plates 36 and an alternate series of carrier support and transfer plates 38 (see FIG. 9) are mounted on main support plate 18 through apertures 40 and are rotated via gear 42 meshing with internal meshing gear teeth 44 of gear 46 which in turn is driven by a system of gears associated with the adjacent carriers. Lastly, the system of gears is driven by motor 16 (see FIG. 1). The gear train is driven through known gear systems to produce rotation of the carrier support and transfer plates as shown, i.e. plates 36 rotating in the counterclockwise direction and plates 38 rotating in the clockwise direction. The carrier support and transfer plates 36, 38 rotate at about 50 to about 500 rpm, preferably 350 rpm.

As the carrier support and transfer plates 36, 38 rotate, each carrier of set 24 is respectively transferred from one support and transfer plate to an "empty" position on the next adjacent support and transfer plate so that each yarn carrier follows a substantially sinusoidal path around main support plate 18. One series of carriers 24 traverses an undulating path from left to right and the other series of carriers 26 traverses an undulating path from right to left intersecting with the first path and 180° out of phase therewith as shown in FIGS. 8 and 9.

Referring to FIG. 9, an exemplary portion of each set of yarn carriers is shown schematically by circles 24, 26 representing the carrier support plates. The first series of yarn carriers are designated from left to right—24A, 24B, 24C, 24D, 24E, and 24F. This series of carriers traverses the undulating path 20 shown by the solid arrows "A" as the carrier support plates 36, 38 rotate. The exemplary carriers of the second series are designated from right to left, 26A, 26B, 26C, 26D, 26E. These carriers traverse an undulating path 22 from right to left as shown by the dotted arrows "B" as the carrier support plates 36, 38 rotate as shown. Thus as the carrier support and transfer plates 36, 38 rotate in opposite directions the "empty" position for each support plate alternates from the 6 o'clock position to the 12 o'clock position and vice versa.

Each carrier is respectively transferred from one carrier support and transfer plate 36, 38 to the next adjacent carrier support and transfer plate while rotating about its own center 90° for each quadrant of rotation. Thus, for example, carrier 26E is positioned at the 12 o'clock position of carrier support plate 36 as shown in FIG. 9. Carrier tie down bolts 25 lie within a line perpendicular to the radius of the main carrier support plate 18. When individual carrier support plate 30 rotates counterclockwise 90° as shown by the dotted arrow, carrier 26E moves to the 9 o'clock position of carrier support and transfer plate 36 and the bolts 25 are directly now in line with the radius of the main carrier support plate 18. Similarly, carrier 24B will have moved to the 12 o'clock position of carrier support plate 38 and the tie bolts 27 will have moved from the orientation shown in FIG. 9 (i.e. in line with a radius of the main carrier support plate 18) to a position perpendicular to the radius. With such movement each carrier 26 moves one quarter circle to the left and each carrier 24 moves one quarter circle to the right. Each quarter circle of rotation is represented by a 90° movement on a sinusoidal path.

As noted, both undulating paths intersect each other and are identical to guide channels 20, 22. As these movements progress, yarn is continuously fed off bobbins 48 which are rotatable on carrier shaft 50. As the undulating movements of carrier support plates 36, 38 progress, the connector shoes 32, 34 of the carriers traverse the respective intersecting guide channels 20, 22. This complex movement results in the formation of an elongated braided product as the rotation continuously takes place and the braid is formed and drawn upward by the take-up roller system to be described.

Figure 2:
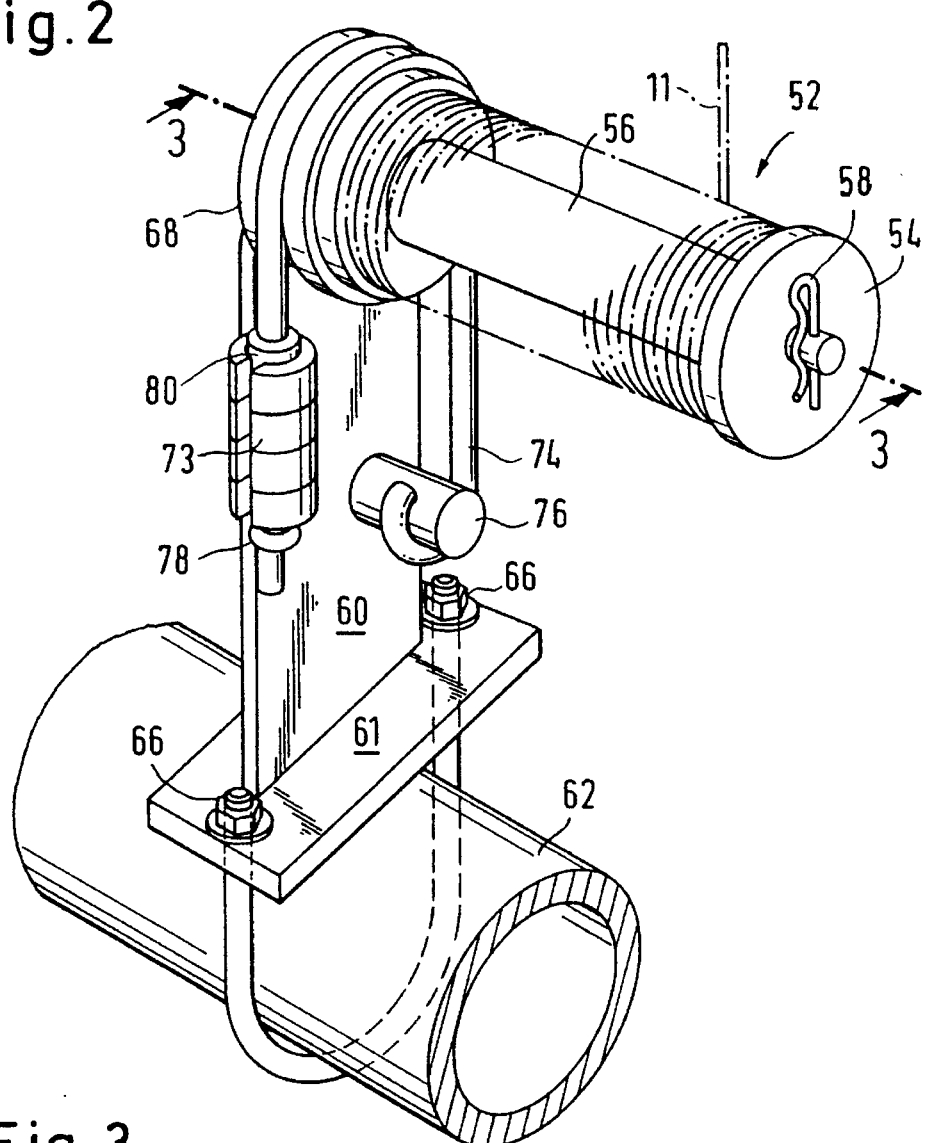
FIG. 2 is a perspective view of the core tensioning system which forms a part of the invention.
Figure 3:
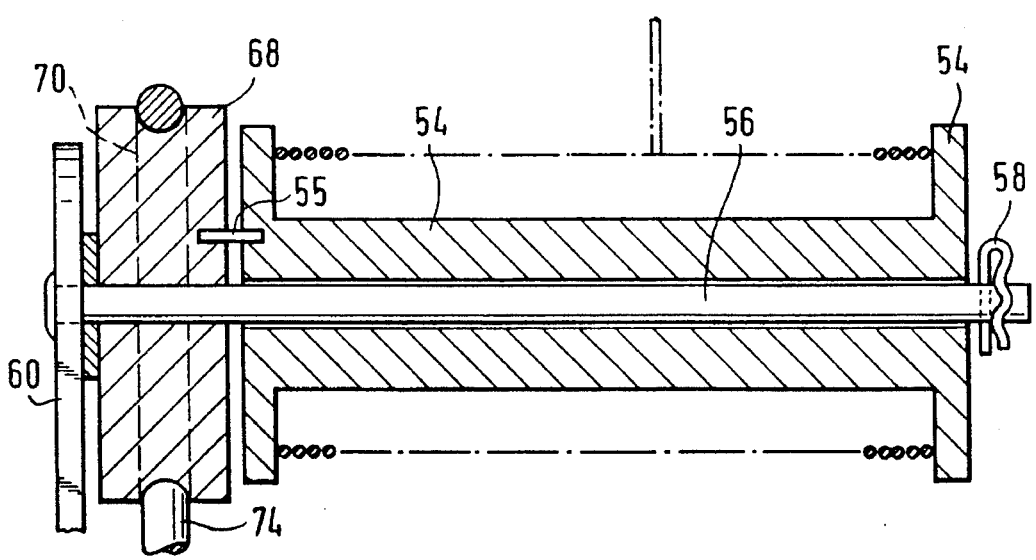
FIG. 3 is a cross-sectional view taken along lines 3—3 of FIG. 2 illustrating the core tensioning system.

Referring now to FIGS. 2 and 3, a unique feature of the present invention is illustrated. The particular type of braided suture contemplated in the present application contains a core yarn surrounded by a system of about 4 to 36 fine denier yarns systematically braided about the core to form a thin sheath. In the preferred suture construction the core possesses a weight which is significantly greater than that of a core of a known suture of equivalent overall denier. Typically, the smallest size braided suture which includes a core would be size 6/0. Such a suture has an overall denier of from about 125 to about 200, and preferably contains a core of about 20–80 denier. Relatively large sutures, i.e. size 1 and 2 sutures having an overall denier of from about 2,000 to 4,000 preferably include a core having a denier in the range of about 800 to 2400. In order to produce a braided yarn suitable for suture applications, the core tension is preferably controlled within a predetermined range to match the tension of the braided outer sheath yarns. FIGS. 2 and 3 illustrate the core tensioning system of the present invention which maintains the tension within this predetermined range. Tension ranges may vary in dependence upon the size of the core yarn.

Referring now to FIG. 2, the core tensioning system 52 is shown and includes supply bobbin 54 containing core yarn 1. Core tensioning must be precisely controlled within a predetermined range to match the tension on the sheath yarns in order to produce a braided product of desired construction, feel and hand.

Bobbin 54 is mounted for free rotation on shaft 56 and retained by cotter pin 58. A vertical support plate 60 is mounted to cross member 62 of the frame 12 by U-shaped clamp 64 secured by nuts 66 to plate 61. The portion of the plate 60 above cross member 62 fixedly supports bobbin shaft 56 as shown.

As can be seen more clearly in FIG. 3, pulley wheel 68 is connected by pin 55 to bobbin 54 for rotation therewith and defines a central groove 70 about which rope 72 is positioned. Rope 72 is connected at one end by "J" shaped hook 74 to fixed pin 76. At the other end of rope 72 is weight carrier 78 positioned for supporting weights 73 of predetermined value. As can be seen, the weight carrier 78 is configured as a central shaft 80 having a weight carrier 78 at the lower end for supporting annular shaped weights 73 shaped as shown similar to a split washer. Thus, as the spool 54 rotates about shaft 56 to feed core yarn to the braiding system the friction drag on the pulley wheel 68 restrains the free rotation of the spool 54 in the downward direction, which is opposite the upward force of the braiding system and braid take-up system. Thus, by adding weights to carrier 78 tension on core yarn 1 may be increased and by removing weights, tension may be decreased. Appropriate core yarn tensions for the preferred braided suture constructions are set out below:

| Suture size | Core Denier | Tension On Core (grams) |
| --- | --- | --- |
| 2 | 800–2400 | 80–90 |
| 1 | 800–2400 | 70–80 |
| 0 | 400–1200 | 50–55 |
| 2/0 | 250–700 | 25–30 |
| 3/0 | 150–300 | 25–30 |
| 4/0 | 80–150 | 20–25 |
| 5/0 | 30–100 | 20–25 |

Referring now to FIGS. 4–7, there is illustrated another aspect of the system for controlling core yarn which forms a part of the present invention. In FIG. 4, there is shown a tension control system 86 which incorporates a core tension.

detector 88 of sufficient sensitivity to detect tension changes in the core yarn 1 and to discontinue the braiding operation in the event the core yarn fails. In particular, prior art braiding apparatus utilized tension detectors of substantially less sensitivity for braiding relatively bulky braids. However, the process of braiding the preferred sutures requires utilization of core yarns having a denier as low as about 20. Therefore, the tension failure value is correspondingly lower than for prior art braids. Accordingly, the present invention incorporates tension detector 88 of sufficient sensitivity to detect core tensions i.e. between about 25 and 80 grams, without placing undue stress on the delicate core yarn which would abrade or break the core yarn. When the core tension exceeds a preset value (i.e., 80 grams), the core yarn will normally fail under tension and cause switch 90 to deactivate electrical power to the apparatus. This permits the operator to investigate the source of the excessive tension and take the requisite steps to correct the problem.

Referring once again to FIGS. 4–6, after the core yarn 1 leaves the tension detector it enters core tube 92 which extends from top plate 16 to approximately ⅔ the vertical distance to the braiding zone. The core tube contains a unique system of ceramic eyelets 94, 98 which are resistant to wear caused by any interaction with the core yarn passing through the tube. Further, the ceramic eyelets 94, 98 present a smooth ceramic surface for the core yarn in instances when the core yarn engages either end of the tube. Thus, the integrity of the fine denier core yarn is maintained in the rare instances where the core yarn shifts laterally and engages one or both ends of the core tube 92. This feature is peculiarly significant to applications of braiding technology to suture production, whereas prior art braiding operations which utilized bulkier components such as cord, ropes, etc., did not require such abrasion proof features. A third ceramic eyelet 95 is provided on bracket 97 which supports the core tension detection system 86.

Figure 10:
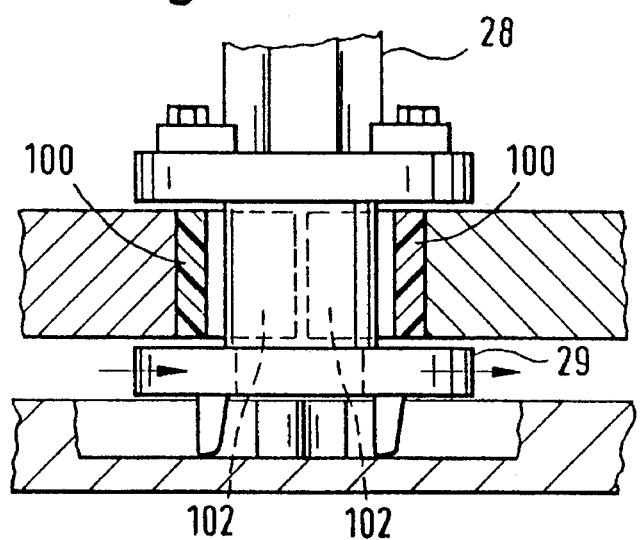
FIG. 10 is a cross-sectional view taken along lines 10—10 of FIG. 9, illustrating the horn gear and noise reduction system shown in FIGS. 8 and 9.

Referring now to FIGS. 10–15, the yarn carrier system and yarn tensioning system is illustrated. Referring initially to FIG. 10, there is shown a cross-sectional view taken along lines 10–10 of FIG. 9 illustrating the base of a carrier 28 at the point of transfer between adjacent support plates 36, 38. Carrier 28 contains carrier support plate 29 which includes downwardly extending connector shoes 32, 34, which extend into guide channels 20, 22 as described previously. The feed 32, 34 traverse the respective guide channel as the yarn carrier is transferred between the respective carrier support plates 36, 38. In order to increase the speed of operation of the braiding apparatus and reduce wear and tear on the apparatus, plastic inserts 100 are provided. Plastic inserts 100 may be made of nylon or other suitable plastic material, and reduce the friction between the carrier and carrier support and transfer plate as the carrier is transferred from each carrier support and transfer plate to the next. Plastic inserts 100 facilitate repeated rapid transfer of shafts 102, of the carriers from one carrier support plate to the next without metal on metal abrasion. The plastic inserts increase operating speed and reliability of the apparatus and decrease wear and tear thereby lengthening the useful life of the apparatus. As an added benefit, plastic inserts 100 reduce the noise level generated by operation of the instrument. Plastic inserts substantially as shown have been incorporated into braiders commercially available from Talleres Ratera, S. A., Barcelona, Spain, since about 1983.

Figure 11:
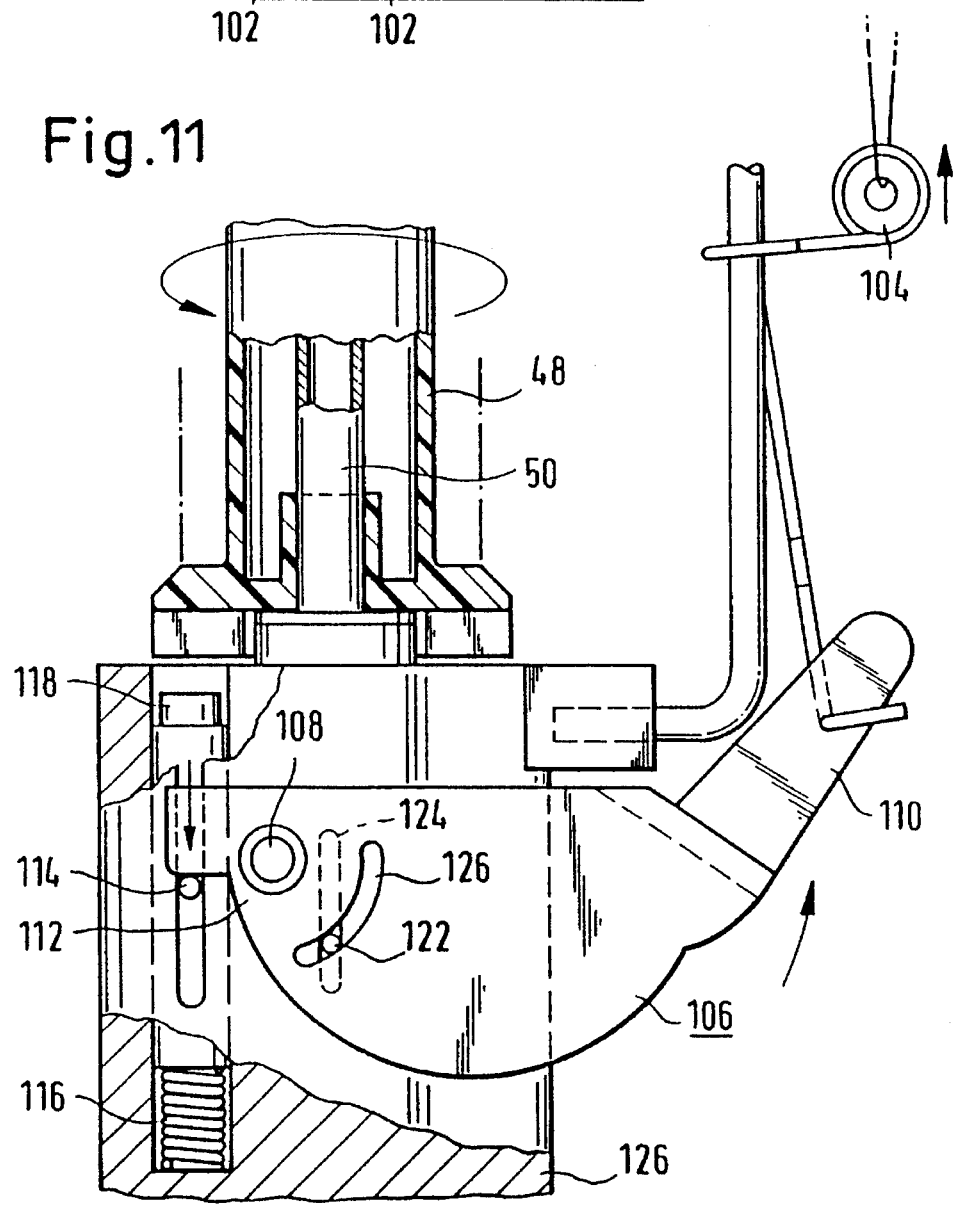
FIG. 11 is an elevational view partially in cross-section, of the carrier yarn tension control system of the invention.
Figure 12:
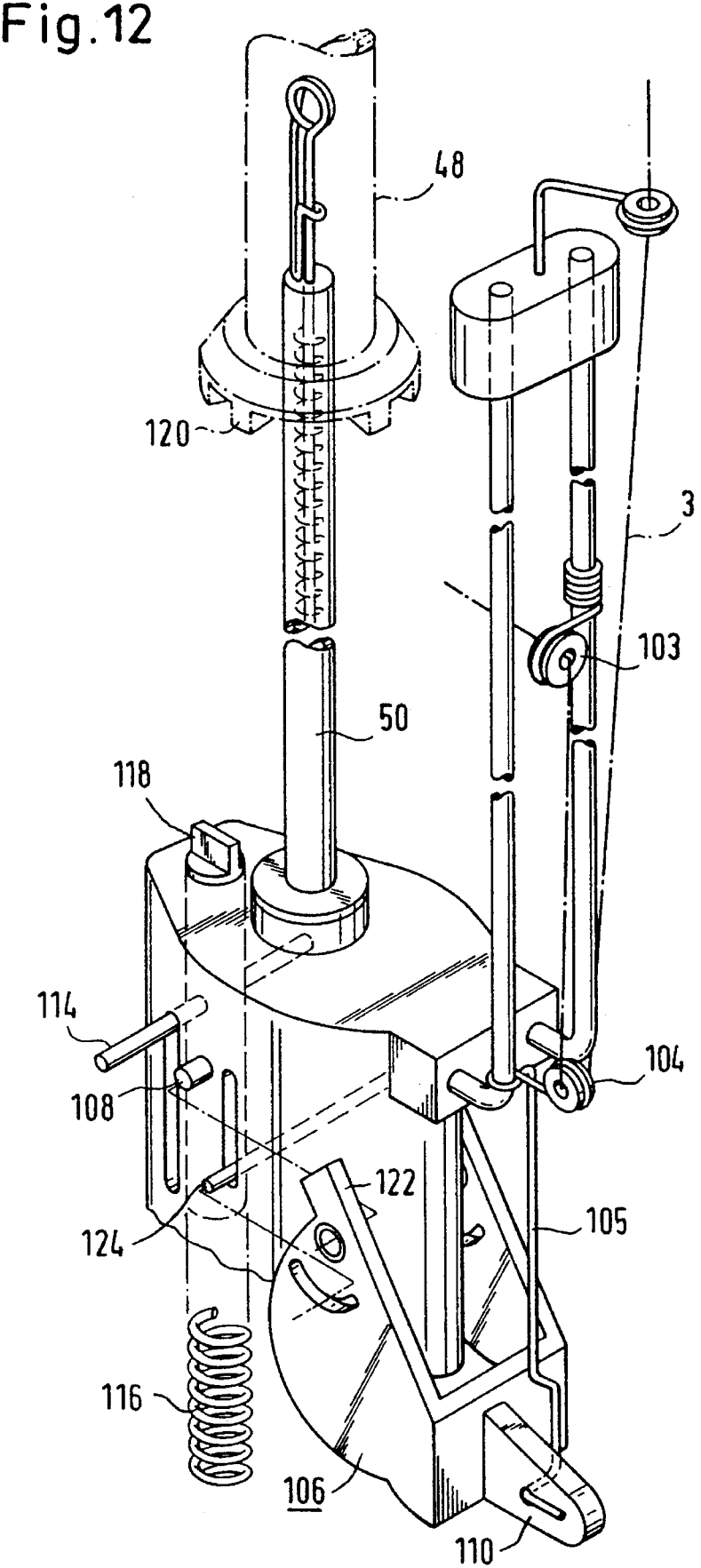
FIG. 12 is a perspective view with parts separated for convenience of illustration, showing the hold down system for the braider bobbin.

Referring now to FIGS. 11–12 a typical carrier is illustrated in further detail. Sheath yarns 3 preferably of between 0.2 and 6.0 denier are dispensed from bobbin 48 where they are directed to ceramic eyelet 103 and then to compensator eyelet 104 connected via rod 105 to compensator arm 106 which automatically compensates to adjust the yarn tension in accordance with braiding needs. The carrier 26 includes compensator arm 106 which pivots about pivot pin 108 as shown. End portion 110 is connected to ceramic eyelet yarn guide 104 while the opposite end portion 112 of pivot arm 106 engages pin 114 which is biased upwardly by light coil spring 116. Pin 114 is connected to pawl 118 arranged to float into and out of engagement with radial slots 120 on the lower surface of yarn bobbin 48 shown in FIG. 12. This structure results in the pivotal bias of compensator arm 106 about pin 108. Pin 122 moves upwardly and downwardly in vertical slot 124 in carrier housing 126 while traversing the moving arcuate slot 127 in compensator arm 106.

In operation, yarn is drawn upwardly by the braiding system, and when the tension of the yarn exceeds a predetermined value the end portion 112 of pivot arm 106 depresses pin 114 against spring 116 causing pawl 118 to withdraw from a slot 12C in the bobbin 48. This permits outfeed of sheath yarn 3 until the tension in the yarn is reduced to a second predetermined value whereby the end portion 112 of pivot arm 106 pivots upwardly under bias of spring 116, permitting pawl 118 to re-enter a radial slot 120 in bobbin 122 thus preventing further outfeed of the sheath yarn 3 until the tension of the braiding take-up increases sufficiently to recycle the compensator arm 106. Thus, the tension of the sheath yarns is controlled within a precise range, particularly by selecting a spring 116 which is within a predetermined range of spring rates. Prior art braiders utilized a spring 116 of significantly greater spring rate than is contemplated herein due to the fact that braiding was accomplished with heavier braiding materials. In addition, in prior art braiders pin 122 was also arranged to be biased downwardly by a spring positioned centrally of shaft 50. In the present apparatus the central spring has been eliminated and spring 116 has been selected to have a reduced spring rate in the range of from about 0.6 to 0.7 pounds per inch, the standard spring on such braiders having a much higher spring rate on the order of about 0.9 to about 1.0 pounds per inch. Reducing the spring rate reduces the tension force on the yarn necessary to cause pivot arm 106 to rotate and withdraw pawl 118 from slot 120, thereby permitting the bobbin to rotate and pay out additional yarn. The reduced spring rate accommodates the relatively lower tensile strength associated with sheath yarns of aforementioned preferred denier range suitable for producing braided sutures. The production of such sutures is thus carefully and precisely controlled to accommodate the fine character, not only of the finished braided suture, but particularly of the yarn components thereof.

Figure 14:
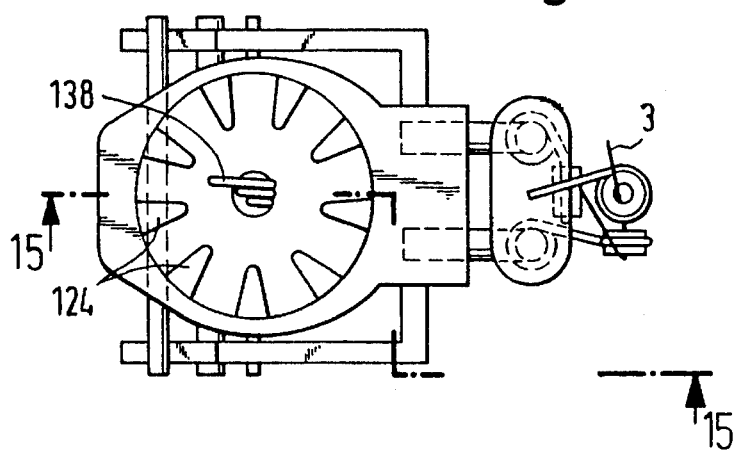
FIG. 14 is a top view of the braider bobbin and carrier system of the invention.
Figure 13:
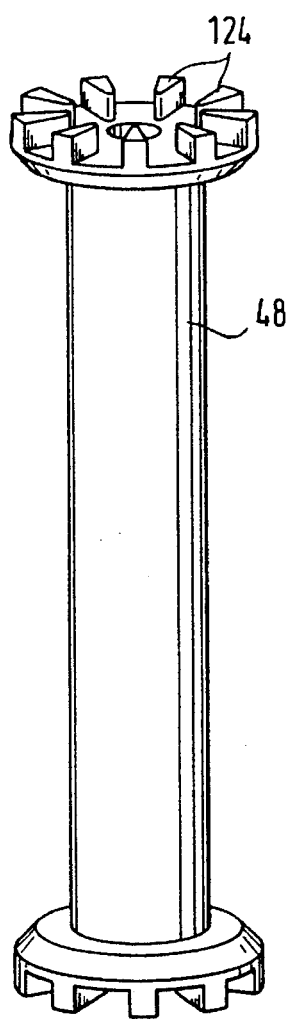
FIG. 13 is a perspective view of the improved braider bobbin constructed according to the invention.
Figure 15:
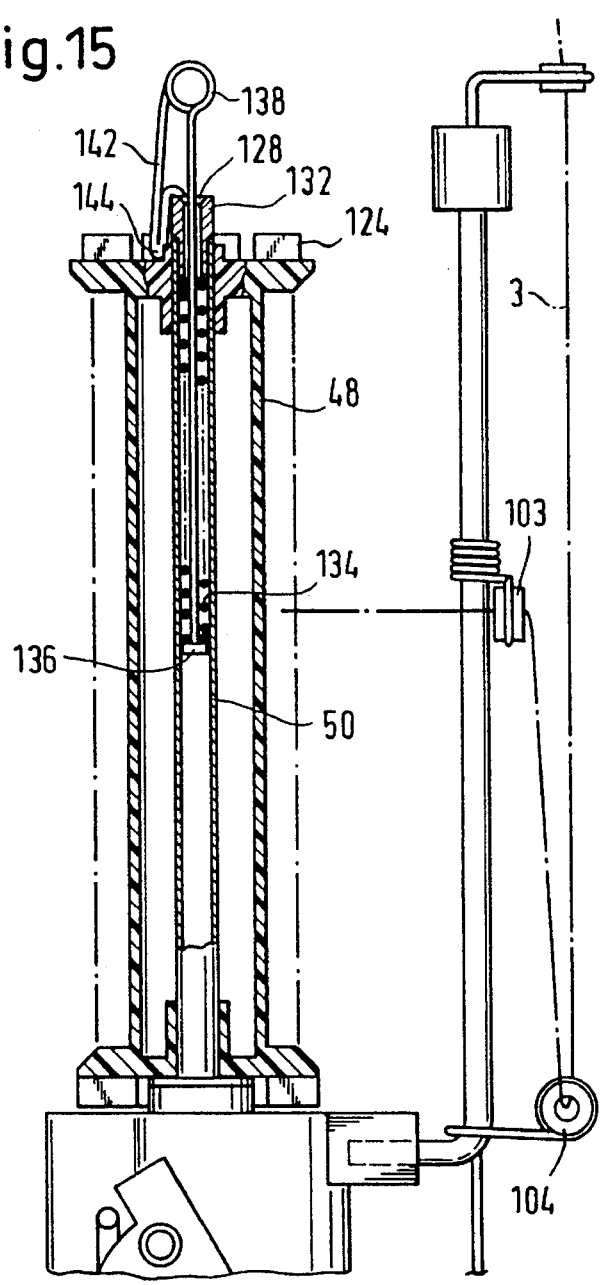
FIG. 15 is a cross-sectional view taken along lines 15—15 of FIG. 14.

Referring now to FIGS. 13–15, the unique yarn dispensing system according to the present invention is disclosed. Bobbin 48 is integrally constructed of a lightweight material such as molded nylon or other plastic material. The bobbin is constructed to have an overall weight of about 20 grams and a minimum diameter dimensioned so as to reduce inertial forces on the delicate sheath yarns. In order to reduce tension on the yarns further, the number of radial segments 124 which control the release point of the bobbin have been reduced to nine segments as shown.

This compares to prior art bobbin and carrier assemblies wherein a metal bobbin is mounted over a shaft. The bobbin engages and is fixed by screw mounting so as not to rotate relative to the top surface of a metal plate on the carrier. The bottom surface of the metal plate has 12 or more segments to engage the carrier pawl. The prior art bobbins are also of smaller diameter than the bobbins of the present invention, and yet weighed about 50 grams. The combined bobbin and adaptor of prior art braiders have a total weight of about 85 grams. The increased diameter and light weight of the present bobbin, together with the integral pawl engaging segments and reduced number thereof, further reduce the force which must be exerted on the yarn in order to unwind the yarn from the bobbin.

In particular, the unique braider bobbin of the present invention is specifically constructed to adapt the apparatus for braiding fine denier yarns applicable to fine sutures and is preferably constructed having the following characteristics:

a) reduced mass integrally molded nylon construction of approximately 20 grams, as compared to prior art bobbins of approximately 50 grams, and prior art bobbin and adaptor assembly weighing about 85 grams;

b) reduced number of pawl engaging segments 124 which are integrally molded with the bobbin, preferably 9 segments, not more than 11, versus prior separate adaptor structures having 12 or more pawl engaging segments and higher mass. This structure produces greater circumferential spacing between segments, permitting improved engagement by pawl 118 at high rotational speeds;

c) bobbin diameter approximately 20mm as compared to lesser diameter prior art bobbins. This feature reduces the tension force on the yarn required to turn the bobbin and stabilizes the bobbin and yarn movements; and d) unitary construction bobbin, injection moldednylon (or other moldable plastic) permitting relatively large diameter bobbin at reduced weight with close tolerances (i.e. ±0.15 mm) for precision in Winding from flange to flange.

Referring now to FIGS. 14 and 15, the unique quick connect/quick release bobbin holder is illustrated. As noted previously, bobbin 48 is constructed of a lightweight moldable material such as nylon and defines a central opening extending the length of the bobbin. The bobbin is positioned about upstanding carrier shaft 50 and secured by top holder 128 as shown. Top holder 128 is comprised of a folded wire clip slidably positioned within collar 132 which is fixedly attached to the top of shaft 50 by known means such as interference fit, threads, adhesives etc. The folded wire clip is biased downwardly by coil spring 134 which is arranged to be compressed by engagement with disc 136 attached to the lower end of clip 128 when the clip is raised upwardly. Clip 128 is looped at the top at 138 to form an arm 142 which is dimensioned to engage the upper end surface of the bobbin 48 to maintain the position of the bobbin on the shaft 50 without interference with the rotation of the bobbin. The clip is preferably constructed of a resilient spring wire which resiliently retains the bent shape imparted to it. Further, it can be seen that arm 142 is preferably dimensioned to extend downwardly sufficient to retain the bobbin in position while being dimensioned to provide a slight space 144 between the lower end portion of arm 142 and the top surface of the bobbin.

Quick positioning and removal of the bobbin is accomplished as follows. Clip 128 is pulled upwardly manually against the bias of spring 134 until the lower end portion of arm 142 folds inwardly under the spring bias of loop 138 and rests atop collar 132. This position permits insertion and/or removal of bobbin 48 onto or from shaft 50. After removing the old bobbin or adding a new bobbin with new yarn supply, clip 128 is manually twisted to cause lateral movement of arm 142 so as to be repositioned atop the bobbin 48 thereby retaining the bobbin in position for operation. Thus, a bobbin may be replaced readily by manual manipulation of the clip 128 as described. In this regard, prior art braiders utilized relatively complex devices to secure bobbins to feed braid components for rope or other braids.

Figure 16:
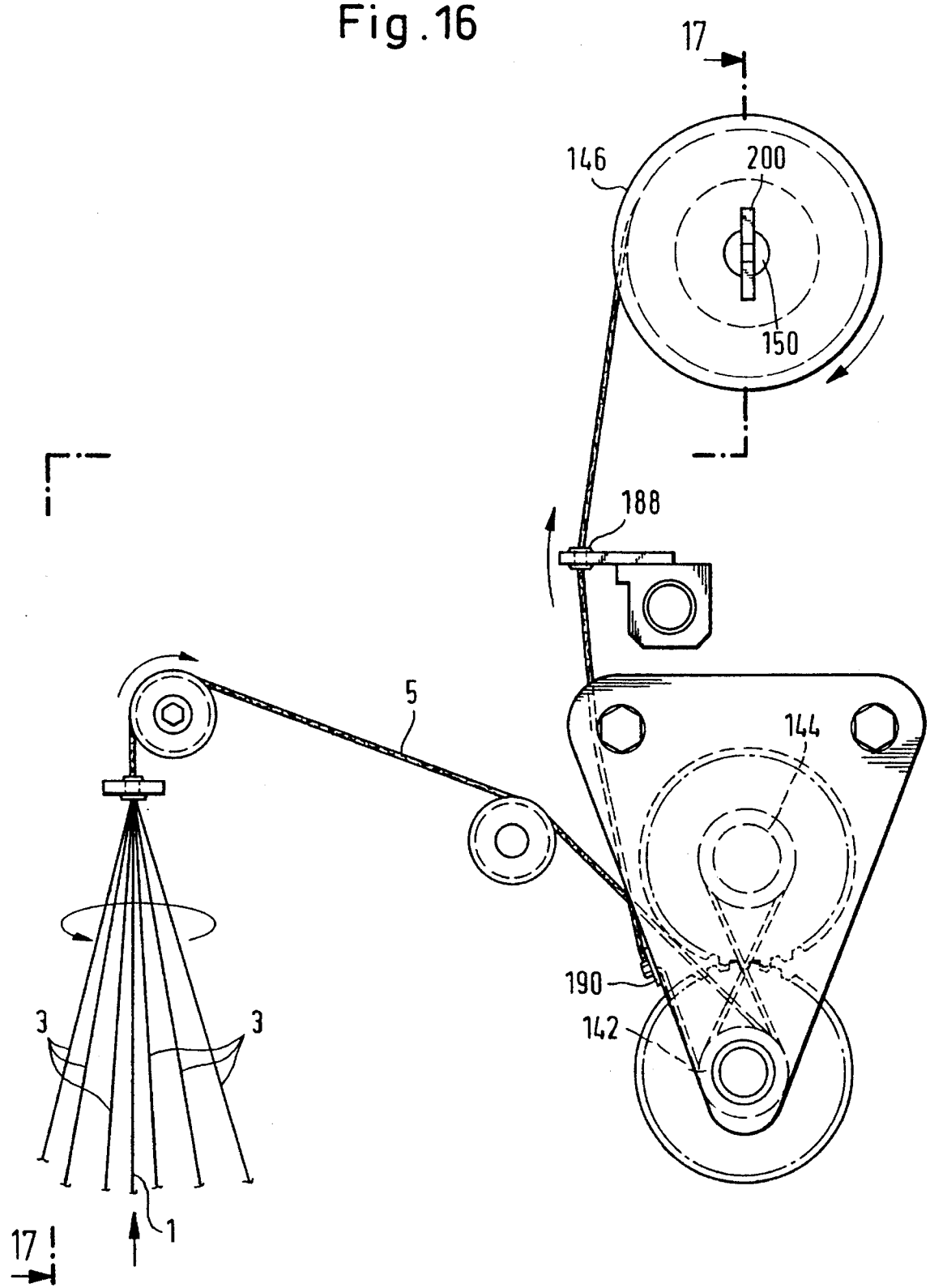
FIG. 16 is a partial schematic view illustrating the path of the yarns and the formation of a braided suture on the present apparatus.

Referring now to FIGS. 16–19, the take-up system for the braided suture product is illustrated. FIG. 16 illustrates the final formation of the braided suture and the take-up roller system leading to final winding of the finished product on take-up spool 146. In particular, core yarn 1 and sheath yarns 3 are formed into a final braided suture 5 which is first directed to take-up "tensioning" rollers 142, 144 and thereafter to final take-up spool 146 where the product is systematically wound in uniform layers about the spool. The braided product 5 is wound continuously about rollers 142, 144 to stabilize the product prior to winding about take-up spool 146. Ceramic eyelets 179, 190 and 188 guide the suture from the braiding zone to the take-up rollers and then to the take-up spool without abrasion or other damage.

Figure 17:
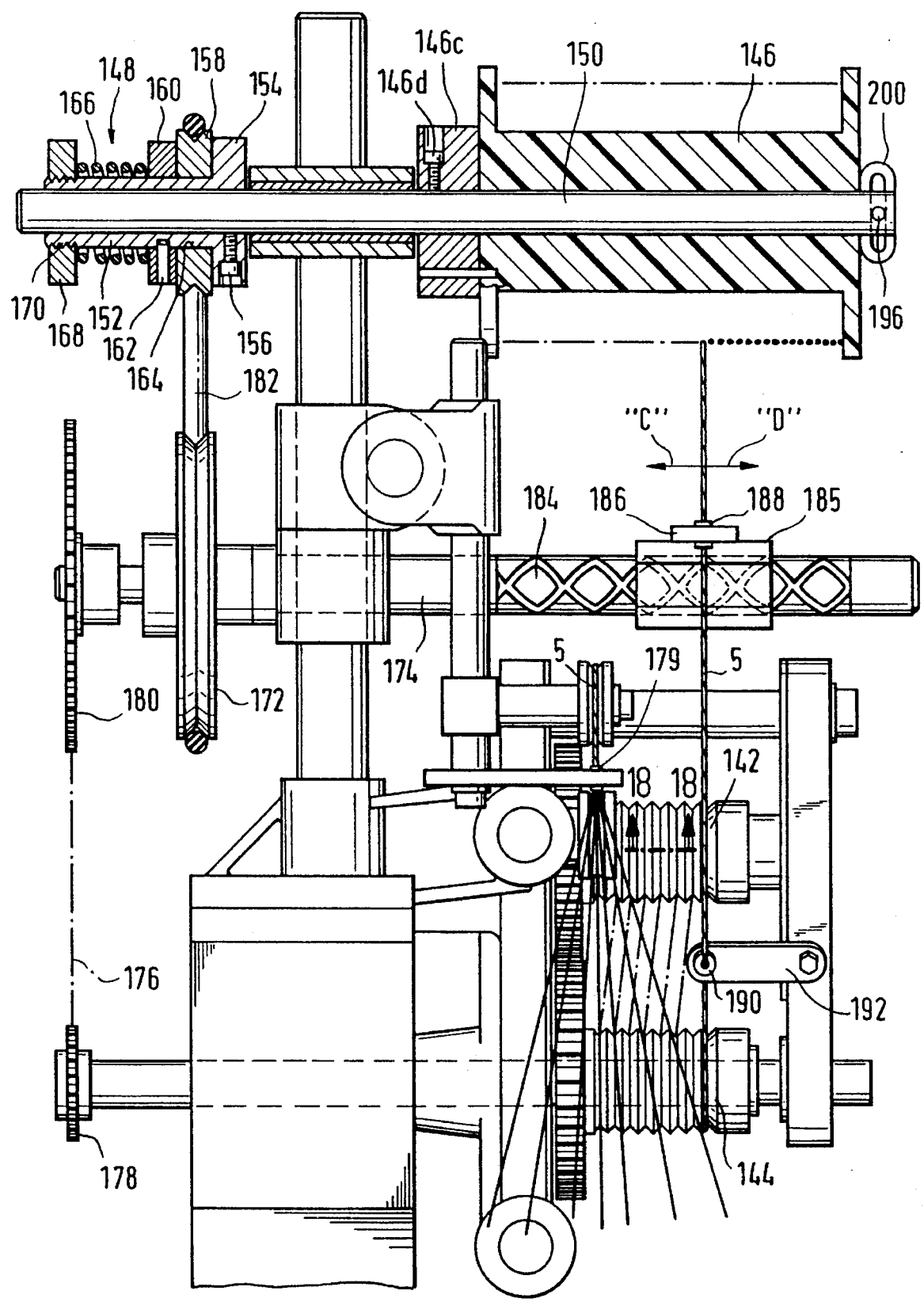
FIG. 17 is a cross-sectional view taken along lines 17—17 of FIG. 16 illustrating the take-up rollers and take-up clutch which form part of the invention.

Take-up clutch 148 is shown in FIG. 17 to precisely control the tension on the finished product via final spool 146. Clutch 148 is mounted on spool shaft 150 and includes internal clutch shaft 152 having first clutch plate 154 at one end secured to shaft 150 by set screw 156 for rotation with the shaft. Molded nylon pulley wheel 158 is slidably positioned over clutch shaft 152 for slidable rotation relative to clutch plate 154. Second clutch plate 160 is connected by screw 162 for rotation with clutch shaft 152. Screw 162 is fitted loosely in a slot (not shown) for movement in the longitudinal direction of shaft 152 to permit clutch plate 160 to move toward and away from pulley wheel 158 by pressure of coil spring 166 when spring 166 is compressed by turning knurled wheel 168 which is fitted by threads 170 about the end of shaft 152 as shown. Thus, by threadedly rotating wheel 168 clockwise to advance the wheel toward the spring 166 the force transmitted by the spring on the clutch plate 160 is increased, thereby increasing the friction forces between pulley wheel 158 and clutch plates 160 and. 154. By turning wheel 168 counterclockwise, the wheel moves outwardly of shaft 152 and the spring force is reduced thereby reducing the friction forces and permitting free rotation of pulley wheel 158.

Referring further to FIG. 17, pulley wheel 172 is connected to shaft 174 which is driven by chain 176 shown schematically in the FIG. Chain 176 is powered by power driven sprocket 178 and thereby produces rotation of shaft 174 via large sprocket 180 at a reduced rate of rotation in accordance with the selected ratio of the size of sprocket 178 to the size of sprocket 180. Pulley wheel 172 is in turn connected to endless drive belt 182 which is fabricated of a suitable, flexible elastomer material and has a circular cross-section and elongated construction.

Referring once again to FIG. 17, shaft 174 contains diamond shaped guide grooves 184 for reception of similarly shaped members formed integrally with product guide member 185 such that continuous rotation of shaft 184 will produce alternating repeating movement of the guide member 185 arranged to move in the direction of arrows "C" and "D" as the shaft 184 rotates. Plate 186 attached to guide member 185 contains ceramic suture guide 188 which guides the finished braided suture received from take-up rollers 142, 144 through ceramic guide 190 affixed to support arm 192 to take-up spool 146.

In operation, as shaft 174 rotates, guide member 185 traverses the right hand portion of the shaft. The guide member 185 alternates from the direction of arrow C to the direction of arrow D in a repeating manner to guide finished braided suture product onto spool 146 in successive uniform and even layers. The tension on the braided suture may be selectively increased or decreased as desired, by turning clutch adjustment knob 168 as described previously. The capability to adjust the tension on the finished product as it is being wound onto spool 146 is significant. As the diameter of the final package increases, the ratio of the linear speeds between the take-up spool 146 and the grooved rollers 142, 144 increases thereby increasing the tension on the finished product. Adjustment of the tension on the finished product is then possible by adjusting clutch 148 to maintain appropriate tension on the suture with a high degree of accuracy and control.

Figure 18:
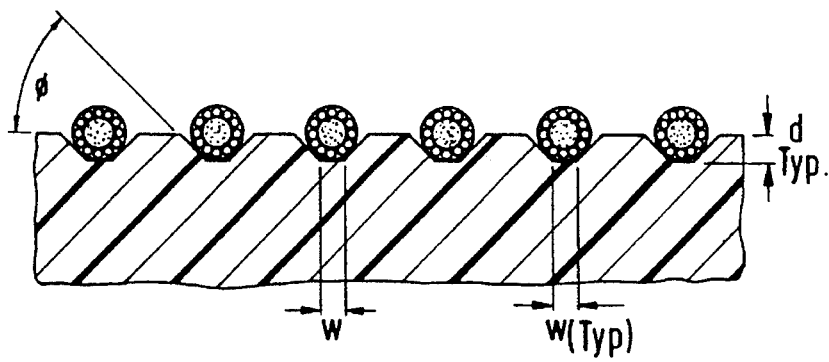
FIG. 18 is a cross-sectional view taken along lines 18—18 of FIG. 17 illustrating the novel take-up spool constructed according to the invention.

Referring once again to FIG. 17 in conjunction with FIG. 18., the braid take-up roller system is illustrated. As can be seen in FIG. 18, the take-up rollers 142, 144 are configured to include relatively sharp "V-shaped" grooves for braided suture take-up to facilitate appropriate contact with braided suture products of a wide range of sizes, including extremely small suture diameters. Further, since the braid is continuously wrapped around the rollers 142, 144, it has been found that it is possible to increase the number of grooves, i.e. wraps, for a given length of rollers, thereby increasing the friction contact between braided suture product and the rollers. This facilitates increased control over the finished braided suture product and minimizes slippage between the suture and the rollers. Preferably, the suture is wound around take-up rollers 142, 144 in a FIG. 8 configuration, as shown in phantom in FIG. 16.

Figure 19:
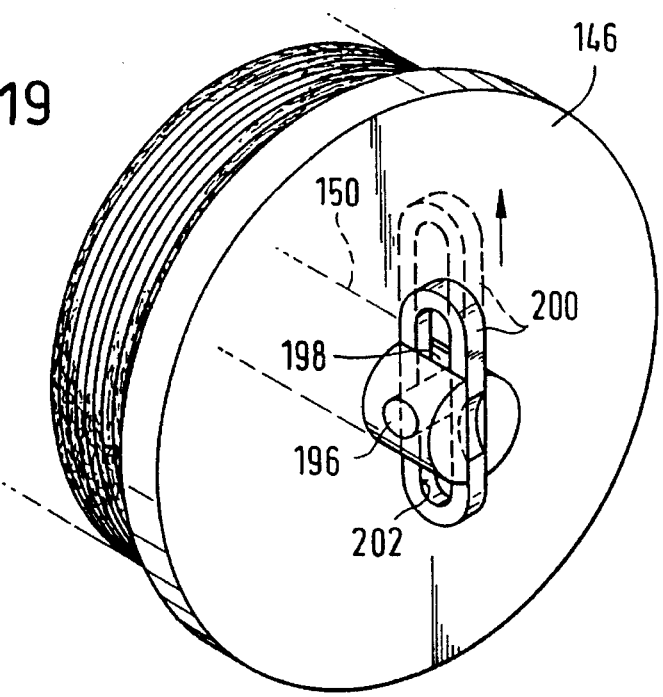
FIG. 19 is a perspective view of the quick-release system in the locked position for retaining the take-up spool on the apparatus of the invention.
Figure 21:
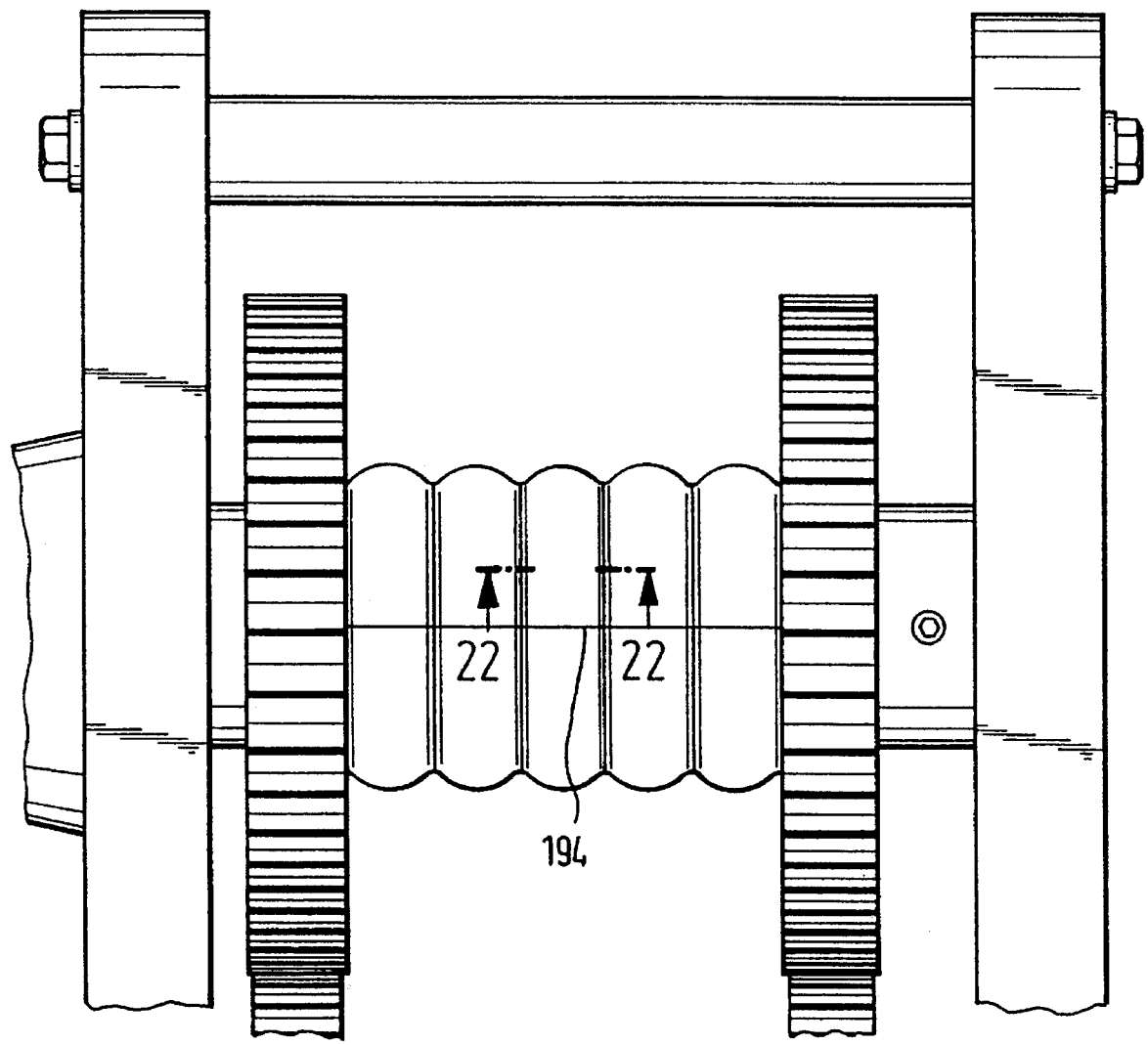
FIG. 21 is an elevational view of a take-up spool constructed according to the prior art.
Figure 22:
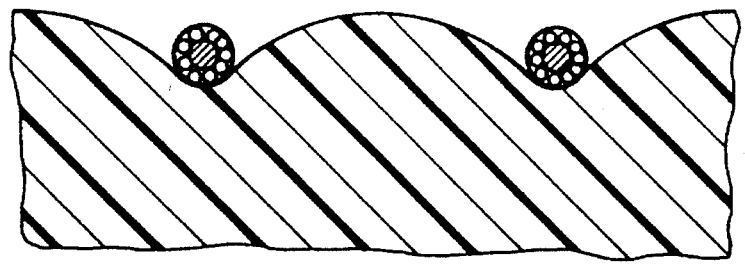
FIG. 22 is a greatly enlarged cross-sectional view taken along lines 22—22, illustrating the surface of the prior art take-up spool of FIG. 21.

As can be seen in comparing the rollers shown in FIGS. 18 and 19 with the prior art rollers (see FIGS. 21 and 22), it will be readily appreciated that the contact between the product and the rollers is increased with the rollers constructed according to the present invention as shown in FIGS. 18 and 19. In addition, it is noted that the take-up rollers constructed according to the invention are of machined plastic material, such as nylon, as opposed to the molded prior art rollers shown in FIGS. 21 and 22. The prior art rollers were of molded construction and included mold part lines 194, an imperfection which does not adversely affect braided products of heavy duty construction, i.e. rope construction; however, the braiding of fine denier sutures as contemplated herein requires take-up rollers of improved construction having smooth surfaces which not only avoid adverse affects on the suture product, but which also produce sufficiently controlled friction to permit take-up of the product without damage. The smooth surfaces of the machined plastic rollers 142, 144 as shown in FIGS. 17 and 18 achieve these objectives.

Referring to FIG. 18, the take-up rollers of the present invention are machined to include grooves having inclined side walls terminating in a flat bottom surface. The overall depth "d" of the groove should be dimensioned to accommodate a range of suture sizes. A depth range of about 0.1 to 0.2 inches may be appropriate, and a depth of about 0.16 inches is preferred. The width of the flat bottom of the groove, shown as dimension "w" in FIG. 18, is preferably about 0.002 inch. The inclined surfaces define an angle O with the outer surface of the take-up roller. It has been found that appropriate angles are within the range 55° to 65° and preferably 60° to 61°.

Figure 20:
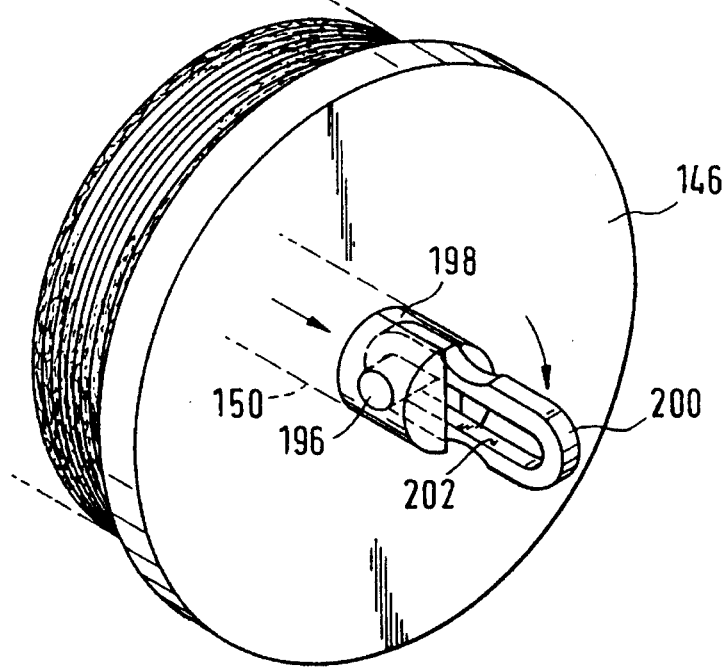
FIG. 20 is a perspective view of the quick release system of FIG. 19 in the release position.

FIGS. 19 and 20 illustrate the quick connect/quick release feature utilized to retain the take-up spool 146 on shaft 150 shown in FIG. 17. Shaft 150 is dimensioned to receive pin 196 and includes a groove 198. A generally endless looped lock member having a cut-out portion 202 shaped to receive pin 196 is positioned within the slot and is rotatable from a position transverse of the shaft 150 as shown in FIG. 19, to a position in alignment with shaft 150 as shown in FIG. 20. The position of lock member 200 shown in FIG. 19 retains the spool 146 on shaft 150 and is secured in position by appropriately dimensioning space 198 relative to pin 196. The position of lock member 200 shown in FIG. 20 permits ready removal of the take-up spool 146 for replacement with an empty spool. Thus, the quick release feature of lock member 200 facilitates ready replacement of a full spool 146. As shown in FIG. 17, member 146c is fixed to shaft 150 by pin 146d. The engagement of pin 146d with shaft 150 restrains spool 146 mounted on shaft 150 against rotation relative to shaft 150.

Figure 23:
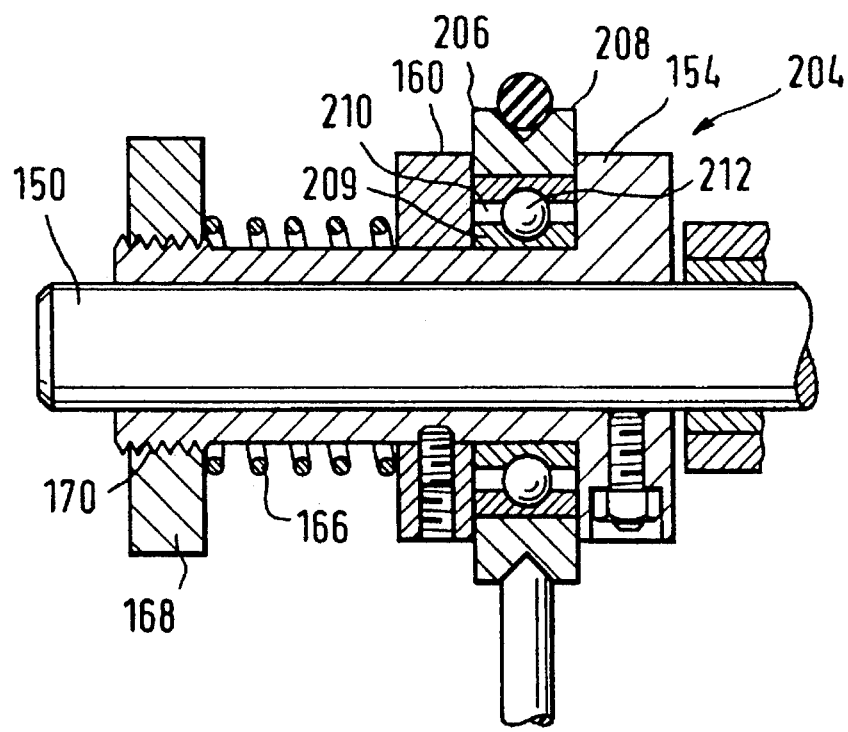
FIG. 23 is a cross-sectional view of the take-up clutch for controlling take-up tension on the finished braided suture.
Figure 24:
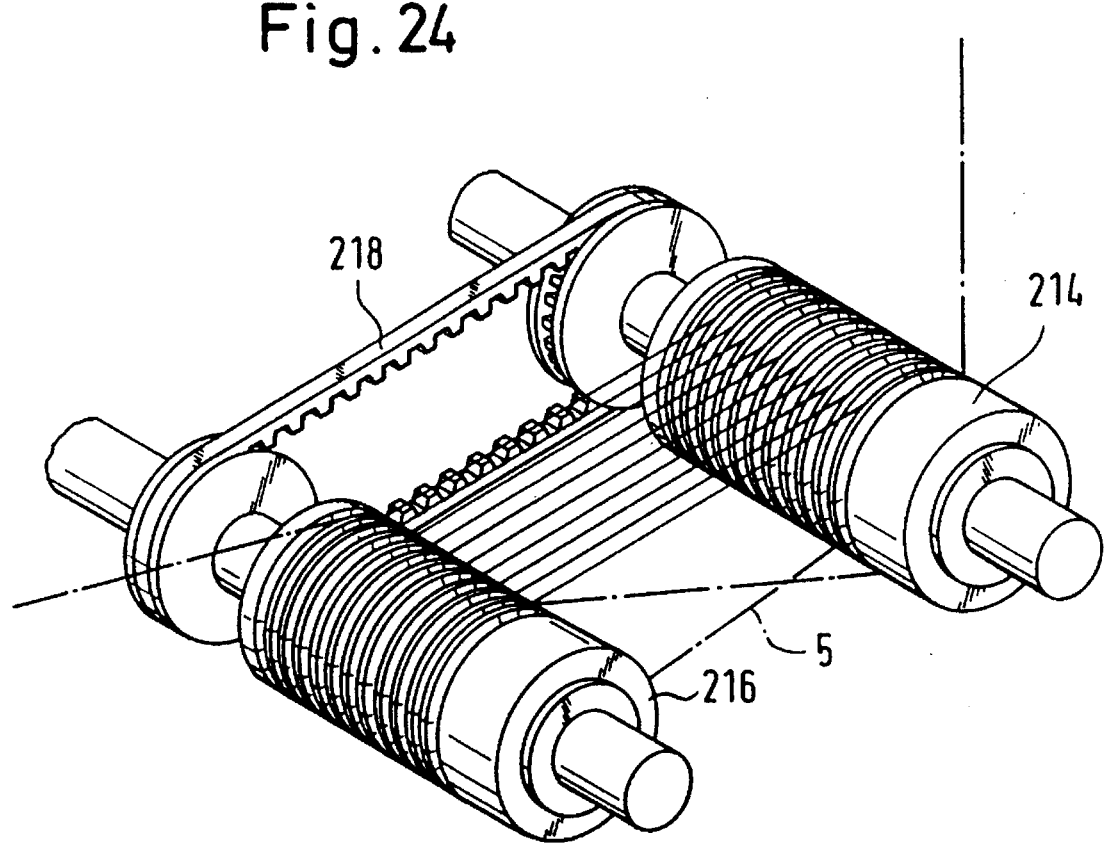
FIG. 24 is a perspective view of an alternate embodiment of the suture take-up rollers of the invention in horizontal tandem positions.

Referring to FIG. 23, an alternate construction of a tensioning take-up clutch is illustrated at 204. Clutch 204 is operative similar to the clutch 148 described previously, but includes split pulley 206 having outer annular portion 208 and inner portion 210 separated by ball bearings 212. Thus, the construction shown permits precise control over the tension exerted on split member 210 by frictional engagement with members 154, 160 independently of friction between split member 210 and clutch shaft 152. The foregoing alternative structure facilitates improved accuracy in the control of the tension exerted on the final braided suture. FIG. 24 illustrates an alternate arrangement for tensioning and take-up rollers 142, 144. In the arrangement shown, rollers 214, 216 are positioned longitudinally and driven by common belt drive 218. Finished braided suture product 5 is shown.

It will be readily appreciated that the features of the present invention as described hereinabove make it possible to produce a fine denier braid capable of application as a suture for surgery. More particularly, the braiding apparatus is well suited for high speed production of consistently high quality final braided suture products having an overall suture denier ranging from as low as about 50 denier to as large as about 4,000 denier. Core yarns will have a preferred denier of from as low as about 20 denier to as high as about 2,400 denier, and sheath yarns will have a denier of from as low as about 0.2 denier to as high as about 6.0 denier.

What is claimed is:

1. An apparatus for braiding fine denier yarns to form a braided suture product which comprises:

a) a frame;

b) a main carrier support plate having a pair of guide channels having an undulating configuration and intersecting each other to define predetermined intersecting paths for guiding a plurality of yarn carriers;

c) a plurality of yarn carriers supported on the main carrier support plate, each yarn carrier adapted for supporting a bobbin for dispensing fine denier yarn made of fine filaments;

d) means for directing the yarn carriers through the predetermined intersecting paths defined by the guide channels;

e) a first yarn guide fixed with respect to each yarn carrier to receive and guide the fine denier yarn from the associated bobbin;

f) a second yarn guide associated with each yarn carrier and positioned and adapted to receive and guide the fine denier yarn from the first yarn guide to the second yarn guide;

g) a third yarn guide positioned and adapted to receive the fine denier yarn from the second yarn guide and to guide the yarn toward the braiding zone;

h) means positioned above the yarn carriers for reception of the yarns in a common braiding zone while the yarn carriers are directed through the intersecting paths to form a braided product from the yarns;

i) means for applying controlled tension to the final braided product while permitting the tension to be transferred to the individual fine denier yarns prior to formation of the final braided suture product;

j) means associated with each second yarn guide to control the tension on the fine denier yarns to about 7 grams or less as the yarn is dispensed from the associated bobbin so as to permit braiding the yarns without breakage of the fine filaments; and k) a pair of take-up rollers positioned downstream of the braiding zone for directing finished braided product toward a take-up spool for winding thereabout.

2. The apparatus for braiding fine denier yarns according to claim 2 wherein each take-up roller defines a grooved surface, the grooved surface having a substantially V-shaped cross-sectional configuration for reception of braided products of a plurality of sizes.

3. The apparatus for braiding fine denier yarns according to claim 2 wherein the grooved surface having a substantially V-shaped cross-sectional configuration terminates in a flat bottom surface.

4. The apparatus for braiding fine denier yarns according to claim 2 wherein the take-up rollers are constructed of a lightweight plastic material.

5. The apparatus for braiding fine denier yarns according to claim 4 wherein the take-up rollers are of machined construction having surfaces substantially devoid of imperfections.

6. An apparatus for braiding fine denier yarns to form a braided suture product which comprises:

a) a frame;

b) means associated with the frame for supporting a plurality of bobbins containing fine denier yarns;

c) means for directing the plurality of bobbins through predetermined paths while dispensing yarn from each bobbin toward a common braiding zone to form an elongated product of braid construction;

d) means to apply tension to the finished braided product and thereby to the fine denier yarns;

e) means to control the applied tension on the fine denier yarns to about 7 grams or less; and f) a pair of take-up rollers positioned downstream of the braiding zone for directing finished braided product toward a take-up spool for winding thereabout, each take-up roller defining a grooved surface having a substantially V-shaped cross-sectional configuration for reception of braided products of a plurality of sizes.

7. The apparatus for braiding fine denier yarns according to claim 6 wherein the means to apply tension to the finished braided product is associated with such take-up spool.

8. The apparatus for braiding fine denier yarns according to claim 7 wherein the take-up rollers are constructed of a lightweight plastic material.

9. The apparatus for braiding fine denier yarns according to claim 8 wherein the take-up rollers are of machined construction having surfaces substantially devoid of imperfections.

10. The apparatus for braiding fine denier yarns according to claim 9 wherein the means to apply tension to the finished braided product is adapted to control the tension on the finished braided product within predetermined limits.

11. An apparatus for continuously braiding fine denier yarns made of fine filaments to form a final braided suture product which comprises:

a) a frame;

b) a plurality of bobbin holders;

c) a bobbin holder support for supporting the plurality of bobbin holders, each holder supporting a bobbin containing fine denier yarn;

d) means for directing the plurality of bobbin holders and the bobbins thorough predetermined paths while dispensing yarn from each bobbin;

e) a first yarn guide fixed with respect to each bobbin holder to receive and guide the fine denier yarn from the bobbin;

f) a second yarn guide associated with each bobbin holder and positioned and adapted for reception and guiding of the fine denier yarn from the first yarn guide toward a common braiding zone;

g) means for applying controlled tension to the final braided product while causing the tension to be transferred to the individual fine denier yarns prior to formation of the final braided suture product;

h) means associated with each second yarn guide to control the tension on the fine denier yarns to about 7 grams or less as the yarn is dispensed from the associated bobbin so as to permit braiding the yarns without breakage of the fine filaments; and i) a pair of take-up rollers positioned downstream of the braiding zone for directing finished braided product toward a take-up spool for braiding thereabout.

12. The apparatus for braiding fine denier yarns according to claim 11 wherein each of the take-up rollers defines a grooved surface, the grooved surface having a V-shaped cross-sectional configuration for reception of braided products of a plurality of sizes.

13. The apparatus for braiding fine denier yarns according to claim 12 wherein the take-up rollers are constructed of a lightweight plastic material.

14. The apparatus for braiding fine denier yarns according to claim 13 wherein the take-up rollers are of machined construction having surfaces substantially devoid of imperfections.

15. An apparatus for braiding fine denier yarns made of filaments of less than 6 denier to form a braided suture product at speeds of 13 to 15 meters per hour, which comprises:

a) a frame;

b) a plurality of yarn carriers associated with the frame, each yarn carrier supporting a bobbin containing yarn made of filaments of less than 6 denier;

c) means for directing the plurality of yarn carriers and the bobbins through predetermined paths while dispensing yarn from each bobbin toward a common braiding zone at a rate sufficient to form 13 to 15 meters of elongated sheath of braided suture product per hour;

d) a first ceramic eyelet yarn guide fixed with respect to each yarn carrier to receive and guide the fine denier yarn from the respective associated bobbin;

e) a take-up spool for receiving the finished braided product, the spool applying controlled tension to the finished braided suture product within predetermined limits and thereby applying tension to the yarns prior to formation of the finished braided suture product so as to permit braiding the yarns in a manner to have a predetermined construction and appearance;

f) a second ceramic eyelet yarn guide associated with each yarn carrier, the second yarn guide receiving and guiding the fine denier yarn from the first yarn guide, the second yarn guide being attached to a pivotal arm at one end, the pivotal arm at the opposite end being in engagement with a pin which engages a coil spring, the pin being attached to a pawl adapted to be selectively received by a corresponding slot in a lower portion of the respective bobbin such that the respective bobbin is prevented from releasing yarn by engagement of the pawl with the slot until the yarn tension exceeds 5 to 7 grams;

g) a third ceramic eyelet yarn guide to receive the yarn from the second yarn guide and to direct the yarn to the common braiding zone; and h) a pair of take-up rollers positioned downstream of the braiding zone for directing finished braided product toward the take-up spool for winding thereabout.

16. A method of braiding fine denier yarns to form a braided suture product which comprises:

a) supporting a plurality of yarns carriers on a frame, each yarn carrier supporting a bobbin containing fine denier yarn made of filaments of less than 6 denier;

b) directing the plurality of yarn carriers and the bobbins through intersecting undulating paths while dispensing yarn from each bobbin toward a common braiding zone at speeds sufficient to form an elongated sheath of braid construction at a rate of 13 to 15 meters per hour;

c) directing the yarn to a first yarn guide fixed with respect to each the yarn carrier;

d) directing the yarn from the first yarn guide to a second yarn guide associated with each yarn carrier and positioned and adapted for reception and guiding of the yarn from the first yarn guide, the second yarn guide being resiliently movable in response to tension of the yarn to control tension on the yarn to about 7 grams or less;

e) directing the yarn from the second resiliently movable yarn guide to a third yarn guide fixed with respect to the yarn carrier whereby the yarn is guided toward the common braiding zone;

f) winding the braided product about a pair of grooved take-up rollers to stabilize the finished braided product;

g) winding the finished braided product about a take-up spool; and h) applying controlled force to the take-up spool and thereby applying controlled tension to the finished braided product within predetermined limits in a manner to transfer the tension to the individual yarns prior to formation of the finished braided product.

17. A method of braiding fine denier yarns to form a braided suture product which comprises:

a) providing a main carrier support plate having a pair of undulating guide channels intersecting each other for guiding a plurality of yarn carriers;

b) supporting a plurality of yarn carriers on the main carrier support plate, each carrier supporting a bobbin for dispensing fine yarn made of filaments of less than 6 denier;

c) directing the yarn carriers over intersecting paths corresponding to the shape of the guide channels, a first set of the carriers being directed in a first direction and a second set of the carriers being directed in the opposite direction, the yarn carriers being directed over the paths at speeds sufficient to form a braided suture product at speeds of 13 to 15 meters per hour;

d) guiding the fine denier yarn from each bobbin by first guide means fixed with respect to the associated yarn carrier;

e) guiding the fine denier yarn by second guide means associated with each yarn carrier;

f) permitting the second guide means to move in response to yarn tension in a manner to dispense yarn from the bobbin in response to tension in the yarn;

g) receiving the yarns in a common braiding zone while the yarn carriers are directed through the intersecting paths to form a braided product from the yarns;

h) stabilizing the braided product by winding the product about a pair of take-up rollers, each take-up roller having a grooved surface for reception of the braided product; and i) winding the stabilized braided product about a take-up spool which applies predetermined tension to each fine denier yarn; and j) controlling the tension on each fine denier yarn to about 7 grams or less; and k) controlling the tension on the braided product to permit formation of a product of predetermined construction and appearance.

18. An apparatus for braiding fine denier yarns to form a braided suture product which comprises:

a) a frame;

b) a main carrier support plate having a pair of undulating guide channels intersecting each other for guiding a plurality of yarn carriers;

c) a plurality of individual carrier support plates positioned on the main carrier support plate, the individual carrier support plates being supported by a plurality of carrier transfer plates positioned adjacent each other and adapted for rotation, each carrier transfer plate being geared for rotation in a direction opposite the direction of rotation of the next adjacent individual carrier support plate and disposed adjacent each other along a circular path, each carrier support plate including at least two downwardly extending guide members dimensioned and configured to be positioned within at least one of the guide channels in the main carrier support plate for guiding the individual carrier support plate and the carrier along a path defined by the guide channel, each individual carrier transfer plate defining four cut-out portions spaced about 90° from each other for reception of a yarn carrier as the individual carrier support plates rotate adjacent each other, each individual carrier support plate being arranged to receive a member attached to at least one of a first set of carriers within a cut-out portion to cause the carrier to travel with the cut-out portion approximately 180° rotation of the carrier transfer plate for transfer of the carrier to a next adjacent individual carrier support plate rotating in a direction opposite the first carrier support plate whereby the carrier traverses an undulating path as defined by one of the guide channels in the main carrier support plate as the carrier is transferred from each carrier transfer plate to the next adjacent carrier transfer plate, each carrier transfer plate being arranged to receive at least one of a second set of carriers within the cut-out portions in a manner to cause each of the second set of carriers to traverse the second of the undulating paths defined by the guide channels in the main carrier support plate such that the second set of yarn carriers traverses a path which intersects with the path followed by the first set of yarn carriers in a direction opposite the first set of carriers;

d) a plastic insert member provided between the carrier transfer plates and the carriers to maintain noise produced by engagement of the transfer plates within predetermined levels;

e) a plurality of yarn carriers supported on the carrier support and transfer plates, each carrier supporting a bobbin for dispensing fine denier yarn;

f) means positioned above the yarn carriers for reception of the yarns in a common braiding zone while the yarn carriers are directed through the intersecting paths to form an elongated braided product from the yarns;

g) means for applying controlled tension to the final braided product while permitting the tension to be transferred to the individual fine denier yarns prior to formation of the final braided product;

h) means for controlling the tension of the final braided product within predetermined ranges to permit formation of a braided product of predetermined construction and appearance; and i) a pair of take-up rollers positioned downstream of the braiding zone for directing finished braided product toward a take-up spool for winding thereabout.

19. The apparatus for braiding fine denier yarns according to claim 18 wherein each take-up roller defines a grooved surface, the grooved surface having a substantially V-shaped cross-sectional configuration for reception of braided products of a plurality of sizes.

20. The apparatus for braiding fine denier yarns according to claim 19 wherein the grooved surface having a substantially V-shaped cross-sectional configuration terminates in a flat bottom surface.

21. The apparatus for braiding fine denier yarns according to claim 20 wherein the take-up rollers are constructed of a lightweight plastic material.

22. The apparatus for braiding fine denier yarns according to claim 21 wherein the take-up rollers are of machined construction having surfaces substantially devoid of imperfections.

23. An apparatus for braiding fine denier yarns to form a braided suture product which comprises:

a) a frame;

b) a main carrier support plate having a pair of undulating guide channels intersecting each other for guiding a plurality of yarn carriers;

c) a plurality of yarn carriers supported on the main carrier support plate, each for supporting a bobbin for dispensing fine denier yarn, the bobbins being rotatable on the yarn carriers for dispensing yarns to a common braiding zone;

d) means for directing the yarn carriers over first and second intersecting paths corresponding to the shape of the guide channels, a first set of the carriers being directed in a first direction along a first of the paths and a second set of the carriers being directed in the opposite direction along a second of the paths;

e) means positioned above the yarn carriers for reception of the yarns in the common braiding zone while the yarn carriers are directed through the intersecting paths to form a braided product from the yarns;

f) means positioned above the braiding zone for reception of the final braided product;

g) means associated with the braided product reception means for applying tension to the final braided product while permitting the tension to be applied to the individual yarns;

h) means on each of the yarn carriers to control the tension of the fine denier yarns to about 7 grams or less as they are dispensed; and i) a pair of take-up rollers positioned downstream of the braiding zone for directing finished braided product toward a take-up spool for winding thereabout.

24. The apparatus for braiding fine denier yarns according to claim 23 wherein each yarn carrier comprises a pivotal arm having yarn guide means for guiding yarn from the bobbin to the braiding zone.

25. The apparatus for braiding fine denier yarns according to claim 24 wherein each such bobbin contains a plurality of radially extending segments positioned at least about the lower surface of the bobbin.

26. The apparatus for braiding fine denier yarns according to claim 25 wherein the pivotal arm is connected to an upstanding pawl arranged to enter into a space defined between the radially extending segments on each bobbin in dependence upon the tension in the yarn so as to prevent rotation of the bobbin in dependence upon the tension in the yarn and to permit withdrawal of the pawl from the space when the yarn tension exceeds a predetermined value.

* * * * *